United States Patent [19]
Thorne et al.

[11] Patent Number: 5,951,582
[45] Date of Patent: Sep. 14, 1999

[54] LANCET APPARATUS AND METHODS

[75] Inventors: David L. Thorne, Kaysville; Gale H. Thorne, Bountiful; Charles V. Owen, Highland; Michael L. Thorne, Bountiful, all of Utah

[73] Assignee: Specialized Health Products, Inc., Bountiful, Utah

[21] Appl. No.: 09/084,112

[22] Filed: May 22, 1998

[51] Int. Cl.⁶ .......................... A61B 17/14; A61B 17/32
[52] U.S. Cl. .......................... 606/182; 606/167; 606/181
[58] Field of Search ..................... 606/167, 181, 606/182, 183, 185; 600/573, 576, 578, 583

[56] References Cited

U.S. PATENT DOCUMENTS

| | | | |
|---|---|---|---|
| 5,476,474 | 12/1995 | Davis et al. | 606/182 |
| 5,514,152 | 5/1996 | Smith | 606/182 |
| 5,571,132 | 11/1996 | Mawhirt et al. | 606/182 |

Primary Examiner—Glenn K. Dawson
Assistant Examiner—Jennifer Maynard
Attorney, Agent, or Firm—Gale H. Thorne

[57] ABSTRACT

A one-time-use, self-powered, restricted entry lancet apparatus which provides a smaller incision in a surface or epidermal layers of a lancing site than in subsurface or dermal layers. Two embodiments of the invention are disclosed. Generally, each embodiment includes a housing, a blade component, a rotary spring and an actuator. The blade generally has a proximal portion and a distal section. The proximal portion is disposed within the housing and is displaced laterally in a first direction during a lancing procedure. During the lancing procedure, the distal section is extended from the housing through an open exit slot and is rotated about an abutment member of the exit slot to be laterally displaced in a direction opposite the first direction. This rotation about the abutment results in an incision pattern which has a smaller cut in the epidermis than in the dermis. Thus, surface trauma is reduced while a broad cut is made in capillary rich regions of the dermal layers.

13 Claims, 25 Drawing Sheets

LANCET APPARATUS AND METHODS

BACKGROUND OF THE INVENTION

1. Field of the Invention

This invention relates generally to lancets and more particularly to novel, self-contained, precooked and single-use lancets which, when activated, extend a tip of a lancet blade outward from a lancet housing and back into the lancet housing for safe disposal.

2. Related Art

In particular, U.S. Pat. No. 5,514,152, issued to Roger E. Smith (Smith) May 7, 1996, discloses a lancet having a cocked torsion spring wound about a centrally disposed hub frangibly connected to a lancet housing. In a plural lancet strip embodiment, the lancet housing is disclosed to be a container for a plurality of lancets, each of which, after use, is frangibly separated from the rest of the strip and individually discarded. The spring is directly interconnected to a lancet blade in a cam/cam follower relationship which is taught to dispose the blade outwardly and inwardly in a substantially linear fashion. When the hub is frangibly separated from the lancet housing, the cocked spring is released to drive a lancet blade tip linearly from the lancet housing and then returned it back into the lancet housing.

Smith discloses frangible separation of the hub from the lancet housing where a base of the hub is annularly connected by sharp corners to the lancet housing. Smith also teaches that stress placed upon the base causes the hub to frange from the lancet housing, permitting a lancing cycle to begin. Before each lancing cycle is initiated, a lancet housing exit is exposed to provide an orifice through which the lancet blade tip travels. It is only when the orifice is provided that the sterility of the package is compromised keeping the blade and internal contents sterile until the orifice is opened.

U.S. Pat. No. 4,643,189 issued to Michael Mintz Feb. 17, 1987 (Mintz) discloses a concept for apparatus for implementing a skin incision which has been applied to a lancet application, particularly to a pediatric lancet, distributed under the name Tenderfoot® by International Technique Corporation, 23 Nevsky Street, Edison, N.J. 08820. This skin incision apparatus comprises a pivotal arm to which a lancing blade is securely affixed and which is driven by a torsion spring. The arm communicates with a surrounding lancet housing at two points, a first point at which is formed a sliding pivot disposed within the lancet housing and a second point which is within a track forming a cam follower arrangement. The arm is driven by the torsion spring to follow the track while sliding transversely to a patient contacting surface through which the blade communicates through a slot in the lancet housing. Thus, a portion of the arm and entire blade moves transversely in the direction of that portion of the arm which resides within the lancet housing between the pivot point and slot. In this manner, an elongated incision, having a controlled depth of cut is made through the surface of the skin. It is important to note that the length of the incision at the skin surface is substantially the same or longer than the length of the cut down below the skin surface, that the pivot is taught to be disposed more than a blade length away from a point of the blade.

In all other known lancets, both safety and non-safety types, it is a common practice to lance the exterior (epidermis) of the skin to reach the capillary rich inner dermis skin layer with an incision which is substantially the same size or greater in the epidermis layer than the subsequent incision in the dermis layer. Of particular interest, in this regard, are the well known facts that there are no blood carrying vessels disposed in the epidermis layer and that the dermis layer generally comprises a capillary rich bed which is the primary target of each lancet.

BRIEF SUMMARY AND OBJECTS OF THE INVENTION

In brief summary, this invention provides novel apparatus and method for single use safety lancets. Rather than a substantially linear incision through both epidermis and dermis layers of skin, devices and methods which are subjects of this instant invention, as exemplified by embodiments disclosed herein, provide a restricted and relatively narrow entry through the epidermis layer coupled with a broader cut below the epidermis layer thereby providing less trauma to the exterior layers of the skin while producing a more extensive cut of controlled depth and breadth in more interiorly disposed layers, which are generally the source of blood acquired by lancing. Generally, the invention employs an extremely narrow blade having a sharpened tip and a cutting edge disposed toward the direction of movement of the blade in the interiorly disposed layers. In this manner, the blade is directed through the epidermis (surface) skin layer, then rotated laterally about a pivot point disposed substantially at the surface of the skin. As a natural consequence, the width of penetration through the essentially blood-free epidermis is effectively the width of the thin blade while the width of the cut in the blood-rich capillary bed of the dermis layers may be several times (e.g. four times) wider than the blade. In this manner an opening sufficient to permit blood acquisition at the skin surface is made through the epidermis while a broader incision is made in the lower dermis to provide a more abundant supply of blood from each lancing procedure.

Though other energy storing, blade driving components may be used within the scope of the invention disclosed herein, a torsion spring is preferred for displacing a blade body, partially disposed within a lancet housing, and, thereby, displacing an associated blade and blade tip angularly out from and back into a lancet housing.

In one embodiment, a blade body comprises a slot into which an axially disposed post of a wound spring is inserted and then released to rotate as the spring unwinds. As the post rotates, the blade and associated blade tip is displaced outward from the lancet housing through an exit portal. The portal comprises a side member, disposed to be in opposition to the direction of blade travel. The side member, resultingly, communicates with and acts as a fulcrum for the blade as it travels outward then inward. Continued travel of the post maintains an edge of the blade against the side member resulting in displacement of the blade tip in a direction opposite the direction of unwinding of the rotary spring and its post. In various other embodiments, the blade body may comprise a substantially circular orifice or an elongated slot through which a torsion spring post is disposed to drive the blade as the spring unwinds. Variation of slot shape and size provides a variety of cut width and depth patterns in sub-epidermal tissue.

Generally, each device lancet housing comprises a top part and a bottom part. In one device embodiment, the bottom part of a housing comprises a hub in which an elongated groove is disposed for the purpose of releasibly retaining a radially disposed arm of the spring which is extended to form the blade driving post. As the post follows a predetermined arc based upon physical characteristics of the spring, post and hub, the blade is displaced through a predetermined pattern as the spring unwinds. Generally, the pattern is predictably significantly more narrow at entry through the epidermis layer than the resultant cut through deeper areas of the dermis layer due to rotation of the blade about the side member.

Further, by providing a track, disposed as a part of the housing and into which the post is inserted to form a guide, a precision pathway is defined for the blade as the spring unwinds. In this manner, a constrained blade tip course may be predictably programmed to accomplish a desired subepidermal cut pattern. As an example, by arcing the guiding track medially inwardly to compensate for distal outward displacement of the post as the spring rotates, a substantially constant cut depth may be accomplished.

Another device embodiment comprises a torsion spring without an associated hub. A spring post is retained in a cocked state by a catch formed in a leading segment of a guide track. To actuate a lancing cycle, the post is offset and released by depressing a lancet trigger. Upon release, the post follows the remainder of the guide track to steer and propagate a blade to make a predetermined cut pattern as described above.

It may be noted that in Smith (as cited above), blade motion comprises a rapidly outwardly driven and then inwardly retracted lancet blade through a cycle which is initiated by franging a hub, securely affixed to a cocked spring, from an integrally associated housing. In Smith also, the blade is constrained to follow a strictly linear in/out path. Such motion produces a cut which is generally at least as large through the epidermis layer of the skin as the resulting deeper cut below the epidermis layer. This is in marked contrast to the cut pattern of the instant invention disclosed herein. Further, in one embodiment, any hub in which the spring is releasibly constrained in this instant invention remains affixed to the housing to provide a more secure support for the spring, before it is released to unwind and drive the blade outwardly and then inwardly.

Note that the guiding process which steers blade action involves a guide track which directly interfaces with a post of a torsion spring and further involves a side of an exit/reentry orifice of the lancet housing. This type of interface with a biasing member is in marked contrast to Mintz wherein an actuator acts directly upon an arm to which is affixed a long incision cutting blade and the spring slidably communicates with the arm.

Accordingly, it is a primary object to provide a lancet having a lancing pattern which comprises an incision which is narrower in the epidermis layer of the skin than a resultant laceration in the dermis layer of the skin.

It is a fundamental object to provide a one-time-use, self-driven lancet having a narrow blade, for facile insertion and narrow incision through an epidermal layer of skin, which is rotated laterally to make a nonlinear laceration through the dermal skin layer following entry through the epidermis layer to produce a broader cut in the dermis layer than the incision made in the epidermis layer.

It is an object to provide a spring and housing combination by which a blade is driven through a predetermined pattern of travel to lance an epidermal layer of skin more narrowly than subsequent lancing of sub-epidermal skin layers.

It is an object to provide a lancet activator system which securely retains the blade inside a surrounding housing before and after a lancing procedure and by which a spring is released to drive the blade through a predetermined skin lancing pattern having a relatively small entry incision through epidermal skin layers and a much larger incision pattern in sub-epidermal layers during the lancing procedure.

These and other objects and features of the present invention will be apparent from the detailed description taken with reference to accompanying drawings.

DETAILED DESCRIPTION OF THE ILLUSTRATED EMBODIMENTS

Figure 1:
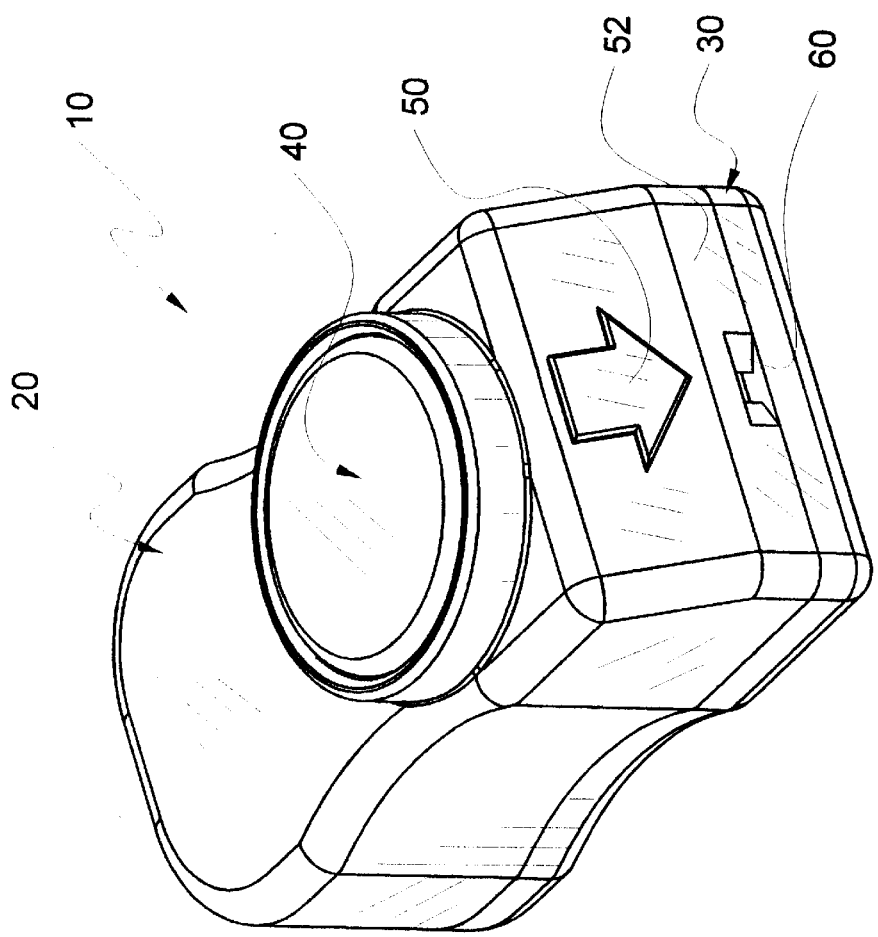
FIG. 1 is a perspective of a single lancet according to the invention.

In this description, the term proximal is used to indicate the segment of a device or other apparatus normally closer to a user when the device is properly used. The term distal, consequently, refers to disposition of a segment of a device which is generally disposed away from the user. Reference is now made to the embodiments illustrated in FIGS. 1–25 wherein like numerals are used to designate like parts throughout.

Reference is made to FIGS. 1–16 wherein a first embodiment is disclosed. As may be noted in FIG. 1, a first single use lancet assembly 10 embodiment comprises a top part 20, a bottom part 30 and an actuator button part 40. Although other kinds of actuators may be used within the scope of the invention, button part 40 may be simply depressed to initiate a one-time lancing cycle. Though optional, an arrow 50 is disposed in close relation to a blade exit slot 60 to permit facile determination by a user of operational orientation of assembly 10. To lance a site (not shown), a surface about the site to be lanced is disposed in close communication with a distal surface 52 of lancet assembly 10. A one-time lancing cycle is initiated by depressing button 40.

Figure 2:
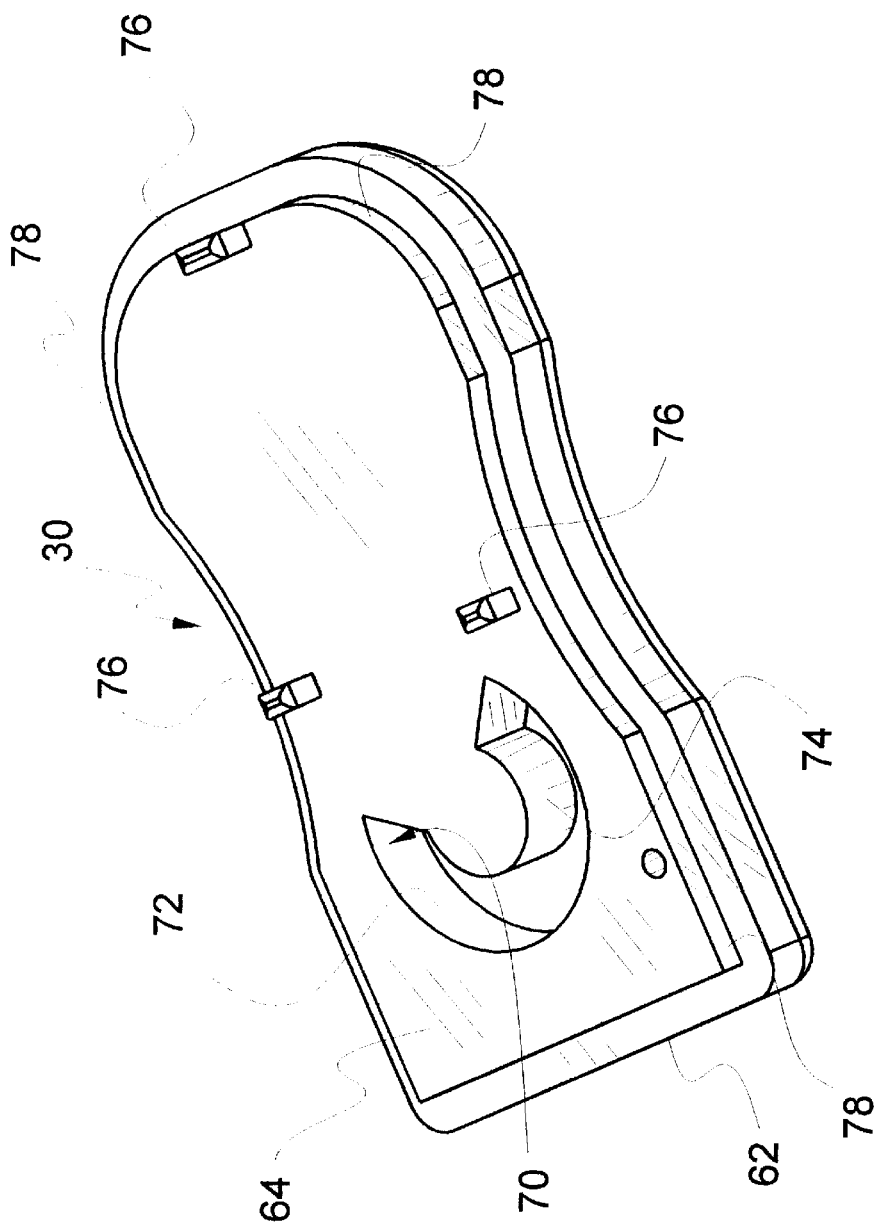
FIG. 2 is a perspective of a bottom part of the single lancet seen in FIG. 1.

Parts 20 and 40 and other internal lancet parts (not seen in FIG. 1) are removed to provide an unimpeded view of the inside portion of bottom part 30 in FIG. 2. Bottom part 30 comprises a substantially planar face 62 which is placed in contact with a site to be lanced. Of course, the curvature of face 62 may be varied to conform with natural interfaces relating to special selected lancing sites, if desired. An internally directed surface 64 is substantially planar to provide a guide plane for a lancet blade (the forced displacement of which is described in detail hereafter). An arcuate channel, disposed in surface 64 and generally numbered 70, comprises guiding edges 72 and 74, the purpose of which is fully disclosed hereafter.

Bottom part 30 comprises a plurality of guideposts 76 which afford precise positioning between parts 20 and 30 when lancet assembly 10 is fabricated. Further, part 30 comprises an arcuate, elongated edge structure 78 which is made to match and thereby provide a sterile seal with a complementary edge structure in part 20 such that assembly 10 may be formed as a self-contained part which maintains an aseptic environment for parts internal to assembly 10. Bottom part 30 (and top part 20) are preferably made from medical injection moldable plastics, such as medical grade polypropylene or polycarbonate. However, other materials may be used within the scope of the invention. Material selected for such use should be resistant to cold flow structure modification and should be relatively non-compressible. Further, if a frangible seal is imposed over exit slot 60, to be broken away before assembly 10 is used in a lancing procedure, a mineral filled polystyrene may be preferred.

Figure 3:
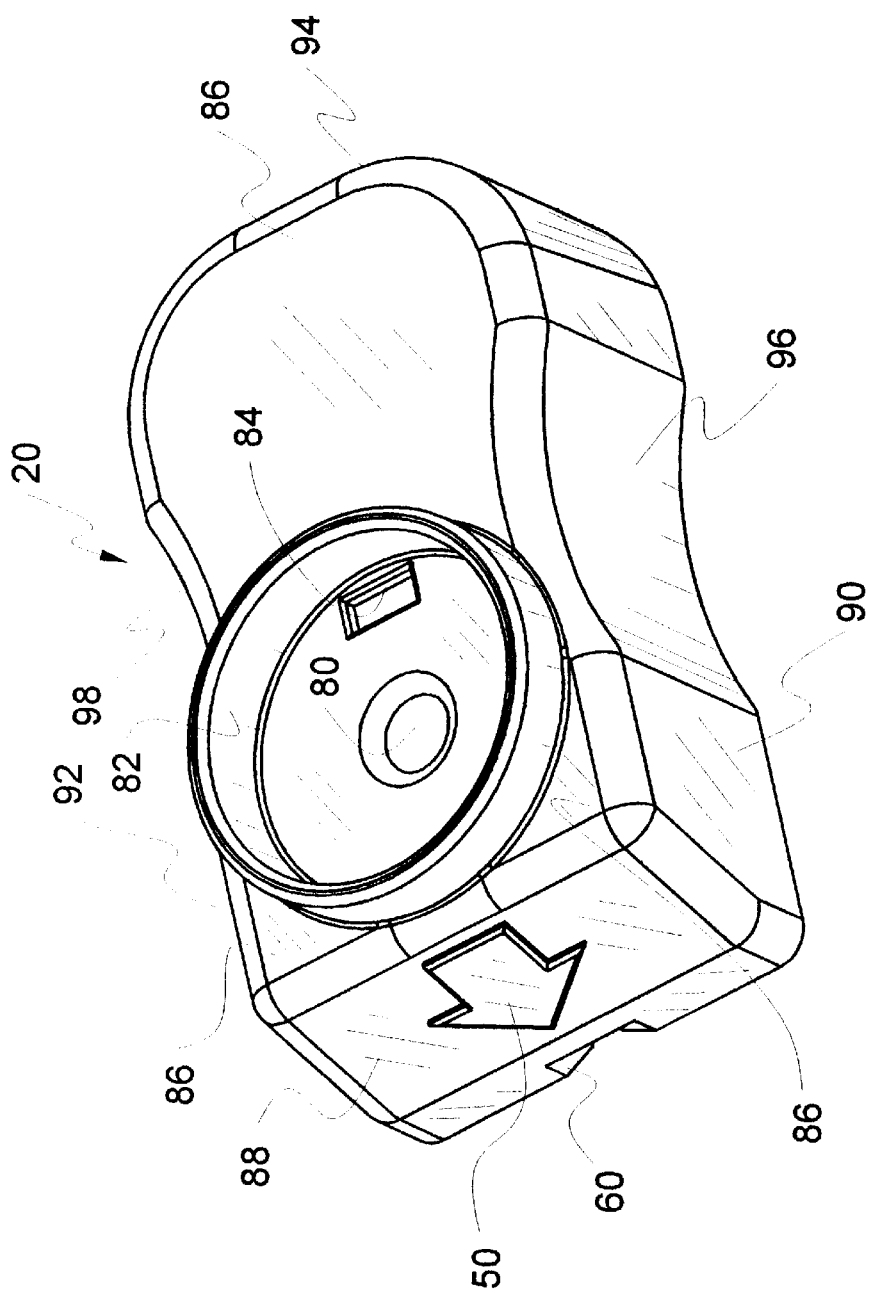
FIG. 3 is a perspective of a top part of the single lancet seen in FIG. 1.

Top part 20 is seen with parts 30 and 40 removed in FIG. 3. Without button part 40, part 20 is seen to comprise an aperture 80 medially disposed in a circular button well 82. Proximally disposed from aperture 80 is a button lock slot 84. Part 20, which is proximally disposed relative to well 82, comprises a substantially planar top surface 86 which proceeds distally to integrally connect to a sloped distal side surface 88. Laterally, side surface 88 is continuous with arcuate side surfaces 90 and 92 which are further joined by a proximal surface 94. Side surfaces 90 and 92 comprise complementary indentations 96 and 98, respectively, which provide gripping surfaces used for facile digital contact during a lancing procedure.

Figure 4:
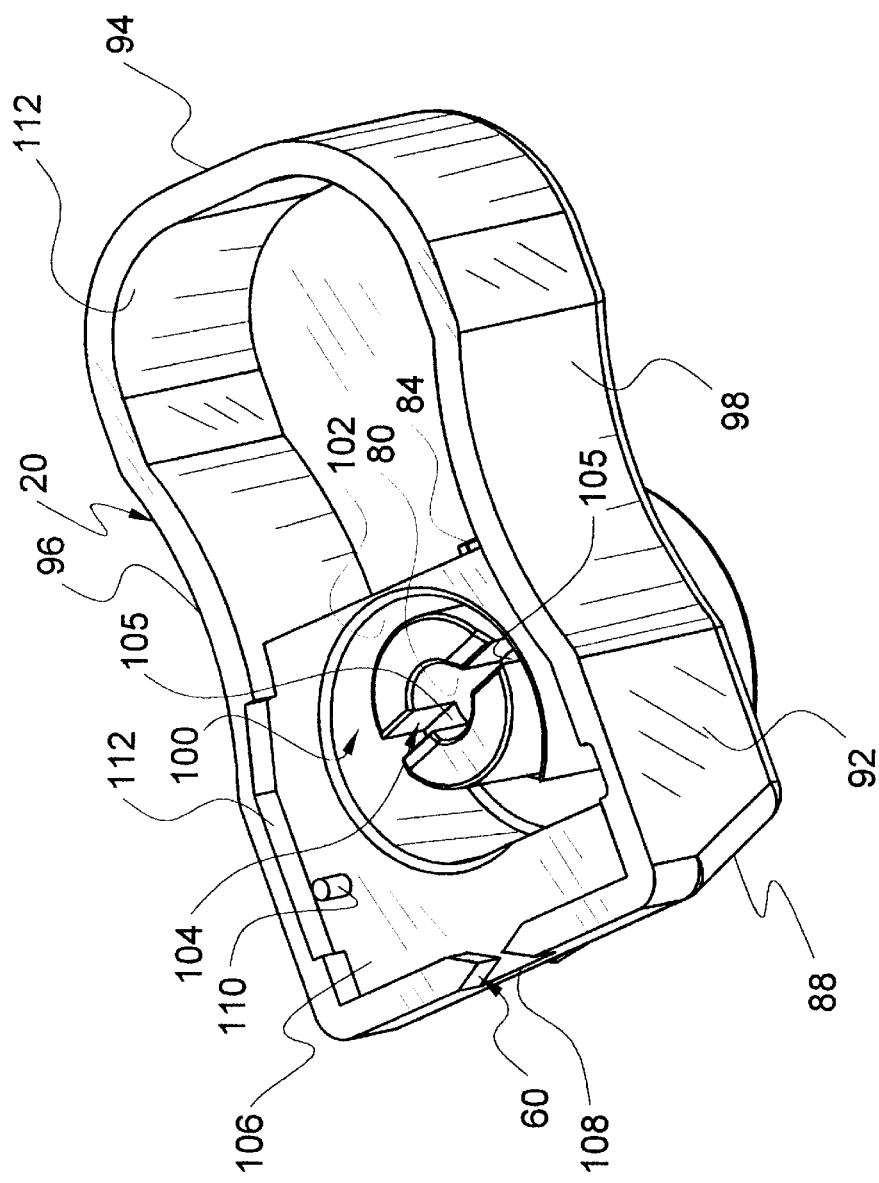
FIG. 4 is an inverted perspective of the top part seen in FIG. 3, wherein an inside view is seen.

An inverted view of part 20 is seen in FIG. 4. Disposed in asymmetrical alignment with well 82 (see FIG. 3), is a hollow spring holding cylinder 100. Disposed within cylinder 100, somewhat proximally from the central axis of cylinder 100, is a spring retention hub 102. Hub 102 comprises a spring arm retention slot 104 disposed across aperture 80. Slot 104 is inferiorly bounded by bottom segments, generally numbered 105, which extend radially outward on each side of aperture 80. A floor 106, from which cylinder 100 subtends, extends distally to form a top segment 108 of exit slot 60. A guide pin 110 protrudes upward from floor 106. The purpose and function of guide pin 110 is clearly disclosed hereafter. Part 20 further comprises an interior wall 112 having a complementary shape to edge structure 78 (see FIG. 2) such that an aseptic seal is provided when parts 20 and 30 are securely affixed. Parts 20 and 30 may be joined by methods and materials well known in plastic adhesion art, such as by ultrasound welding, adhesives or thermal welding.

Figure 5:
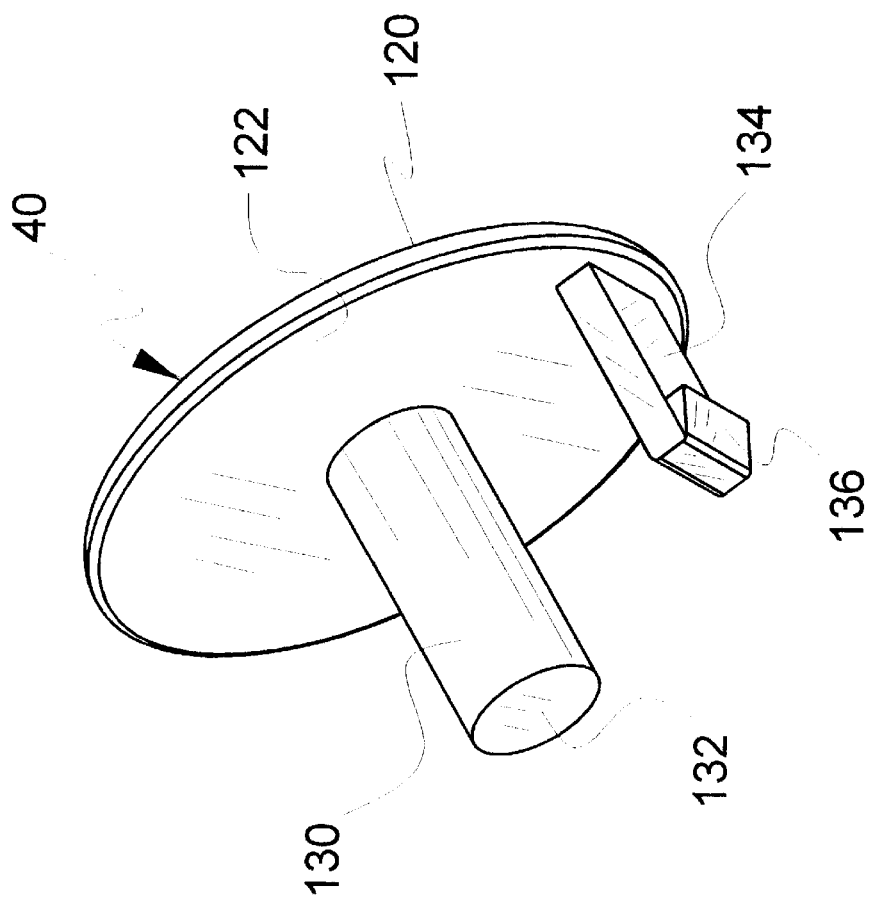
FIG. 5 is a perspective of an actuator button of the single lancet seen in FIG. 1.

One embodiment of button part 40 is seen in FIG. 5. It is preferred that button part 40 have a button 120 which provides a large area to reduce digitary pressure required to initiate a lancing procedure. Extending from a bottom face 122 of button 120 is an elongated stem 130 which is abruptly truncated at surface 132 which is disposed at a level which is even with bottom segments 105 (see FIG. 4) at the bottom of spring retention slot 104 until assembly 10 is used in a lancing procedure. Of course, sufficient clearance must be maintained within well 82 for button stem surface 132 to be displaced from the level of bottom segment 105 to essentially clear slot 104 of a spring arm residing therein. It should be noted that button 120 is preferably made from an essentially incompressible, yet somewhat flexible synthetic resinous material, such as polypropylene.

It is critical that button part 40 be securely affixed to assembly 10. For this purpose, a locking leg 134 is provided. Leg 134 comprises a latch 136 which is inserted through lock slot 84 (see FIGS. 3 and 4) which forms a secure catch. Leg 134 may be replaced by a bulbous section (not shown), molded about stem 130 and a complementary ledge in aperture 80 (also not shown) which permits stem 130 to be forced into aperture 80 relatively easily, but not easily removed therefrom. Such latching and catching connections are known in the plastics molding art.

Figure 6:
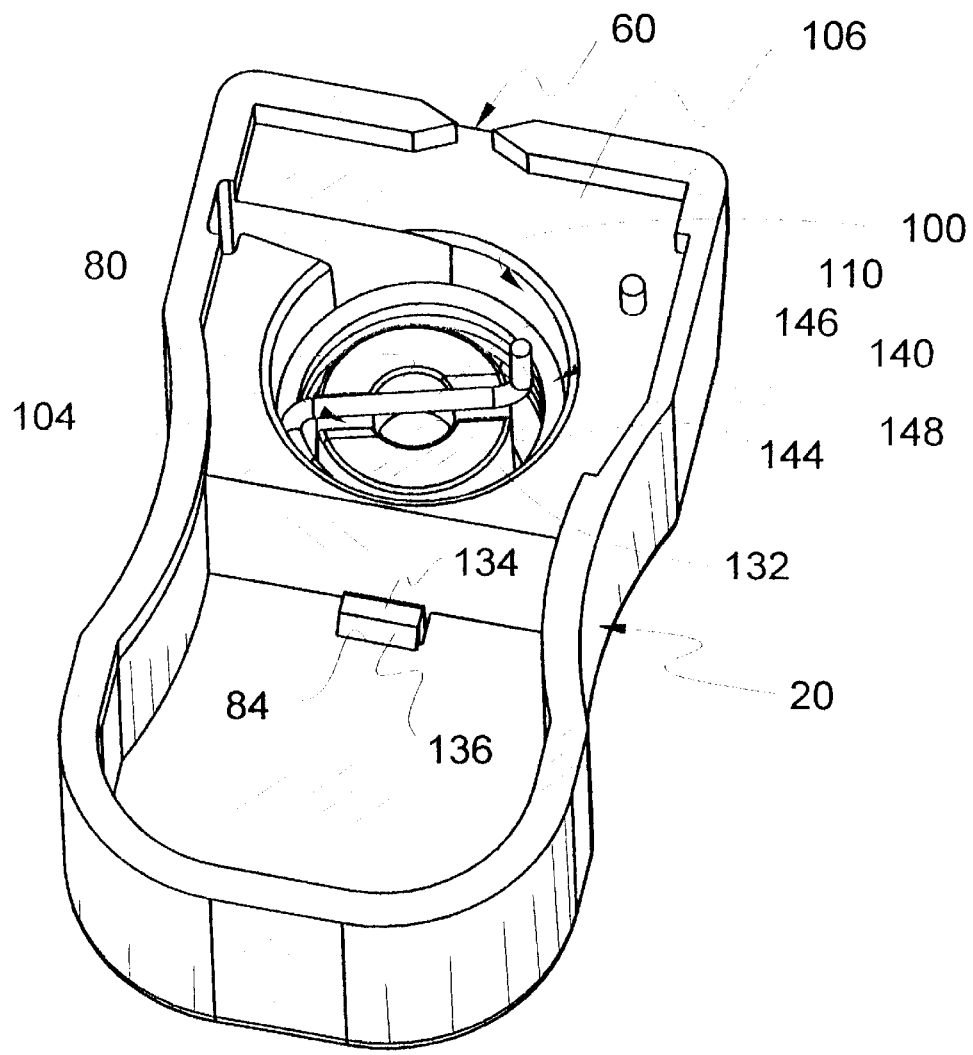
FIG. 6 is an inverted perspective of the top part seen in FIG. 3 showing an internal view of the top part and a cocked spring disposed therein.
Figure 7:
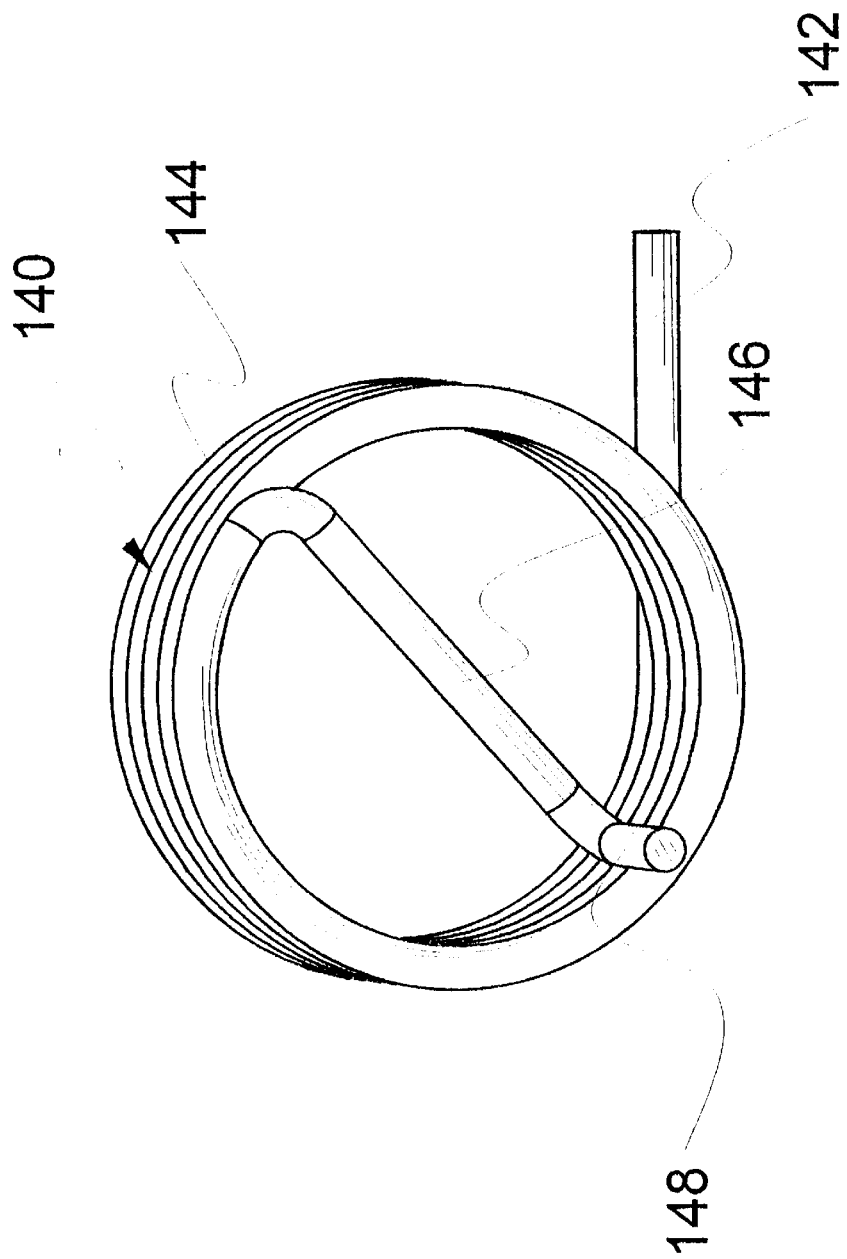
FIG. 7 is a magnified perspective of the spring seen in FIG. 6.

Attention is now directed to FIG. 6 wherein button part 40 stem 130 is inserted into aperture 80 and a torsion spring 140 is disposed in cylinder 100. As better seen in FIG. 7, spring 140 comprises an elongated base extension 142, a coil 144 and a cross-arm 146. Cross-arm 146 further comprises an upwardly distending post 148. Spring 140 is preferably made from 0.023 inch in diameter stainless steel or silicone lubricated piano wire.

Referring once more to FIG. 6, spring 140 is seen disposed in cylinder 100 in a wound state with cross-arm 146 located in a position ready for insertion into slot 104. Relative to floor 106, post 148 is superiorly directed. Note also that latch leg 134 is disposed through slot 84 to catch latch 136 thereat.

Figure 8:
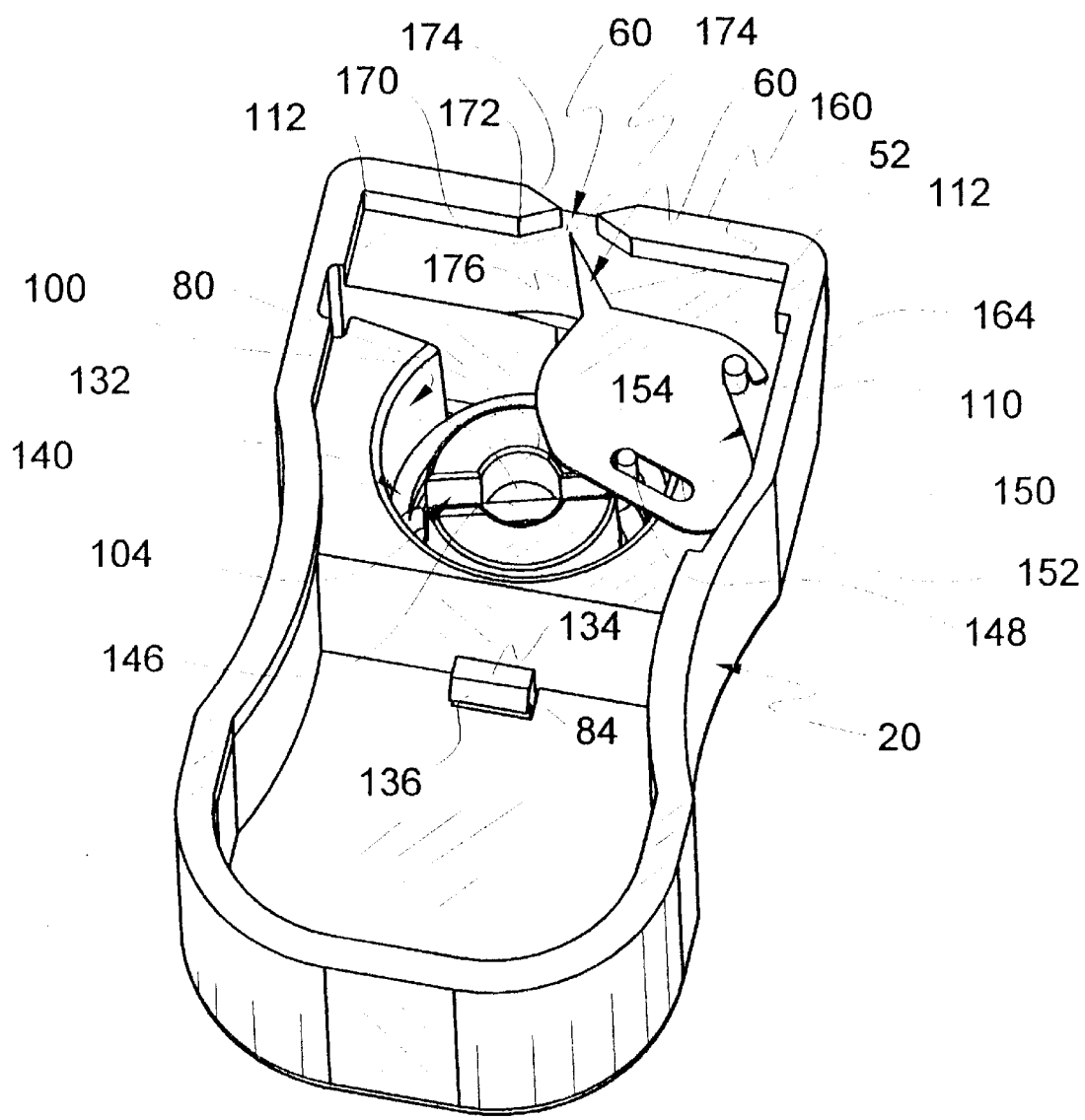
FIG. 8 is a perspective of the parts seen in FIG. 6 with a blade affixed to a post of the cocked spring.

In FIG. 8, cross-arm 146 of spring 140 is disposed and thereby cocked in slot 104. Further, a lancet blade 150 is hingeably affixed to spring 140 via insertion of post 148 through an elongated slot 152.

Figure 9:
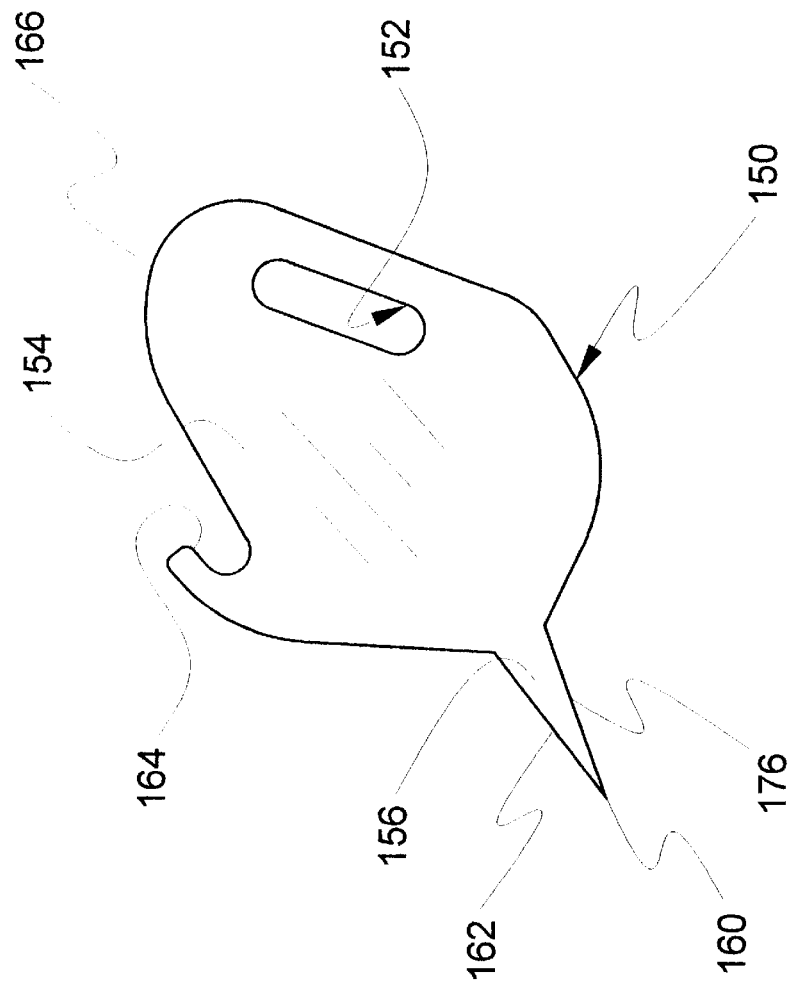
FIG. 9 is a magnified top elevation view of the blade seen in FIG. 8.

In FIG. 9, lancet blade 150 is seen to comprise an arcuately shaped body portion 154 and a blade segment 156. Blade segment 156 comprises a sharpened point 160 and a sharpened edge 162. Body portion 154 is integrally connected to blade segment 156 and in addition to slot 152, by which lancet blade 150 communicates with a rotating crossarm 146 through post 148 as spring 140 unwinds, on one side, body portion 154 comprises a guide hook 164 which is releasibly affixed to guide pin 110 (see FIG. 8) to direct the sharpened point 160 of blade segment 156 through exit slot 60 (also see FIG. 8) at the beginning of a lancing procedure. Sharpened point 160 should have a sufficient degree of sharpness to facilitate entry into a site to be lanced. Also, sharpened edge 162 should be sufficiently sharp to incise an extended length of tissue as blade segment 156 is rotated in the direction of edge 162.

Lancet blade 150 is preferably made from medical grade stainless steel having a thickness of 0.006 to 0.012 inches, although different blade thicknesses may be used within the scope of the instant invention disclosed herein. Blade 150 may be made by a number of processes including machining and laser cutting. However, to make a blade at reduced cost, it is preferable to make the blade by coining. A coined blade has a sufficiently sharp point and cutting edge to provide a substantially painless high velocity incision, such as an incision driven by spring 140.

Although the scope of invention, regarding design of lancet blade 150, provides opportunity for a vast number of blade designs, care must be taken to consider a number of variables. First, the cutting blade segment 156 should have as small a width as possible, precluding blades which are too small in width which might result in blade bending or knurling during a lancing procedure. Selection of material which defines blade thickness is also important. Material which is too thin may result in reduced blood flow due to a restricted blood acquisition path and more rapid clotting than desired.

As is evident in FIG. 8, lancet blade 150 is secured in place prior to release and activation of torsion spring 140 by interaction between guide pin 110 and guide hook 164, post 148 and slot 152, and interior wall 112 of top part 20 and an edge 166 of blade body portion 154 (see FIG. 9) which restricts rotation of lancet blade 150 until post 148 is freed to travel. So disposed, blade 150 is held immobile until arm 146 is ejected from retention slot 104 which, of course, is accomplished by pressing button 40 inwardly into part 20 and forcing stem surface 132 against arm 146.

An important feature of device 10 is seen at that portion of exit 60 which is formed by part 20. At exit 60, part 20 comprises an abutment 170 which opposes direction of travel of post 148 and blade segment 156 as spring 140 unwinds. Abutment 170 is preferably relatively sharp and knifelike, being formed by a pair of intersecting sides 172 and 174 which are disposed to be free of conflict with an anterior edge 176 of blade segment 156 during a lancing procedure. Further, sharpened point 160 of blade segment 156 is steered, by action of arm 146 through post 148 in slot 152 and guide pin 110 in guide hook 164, obliquely through slot 60. Consequent to the direction of rotation of post 148, anterior edge 176 is forced against abutment 170 which acts as a fulcrum about which blade segment 156 rotates until sharpened point 160 is withdrawn from slot 60 at the end of a lancing cycle.

Figure 10:
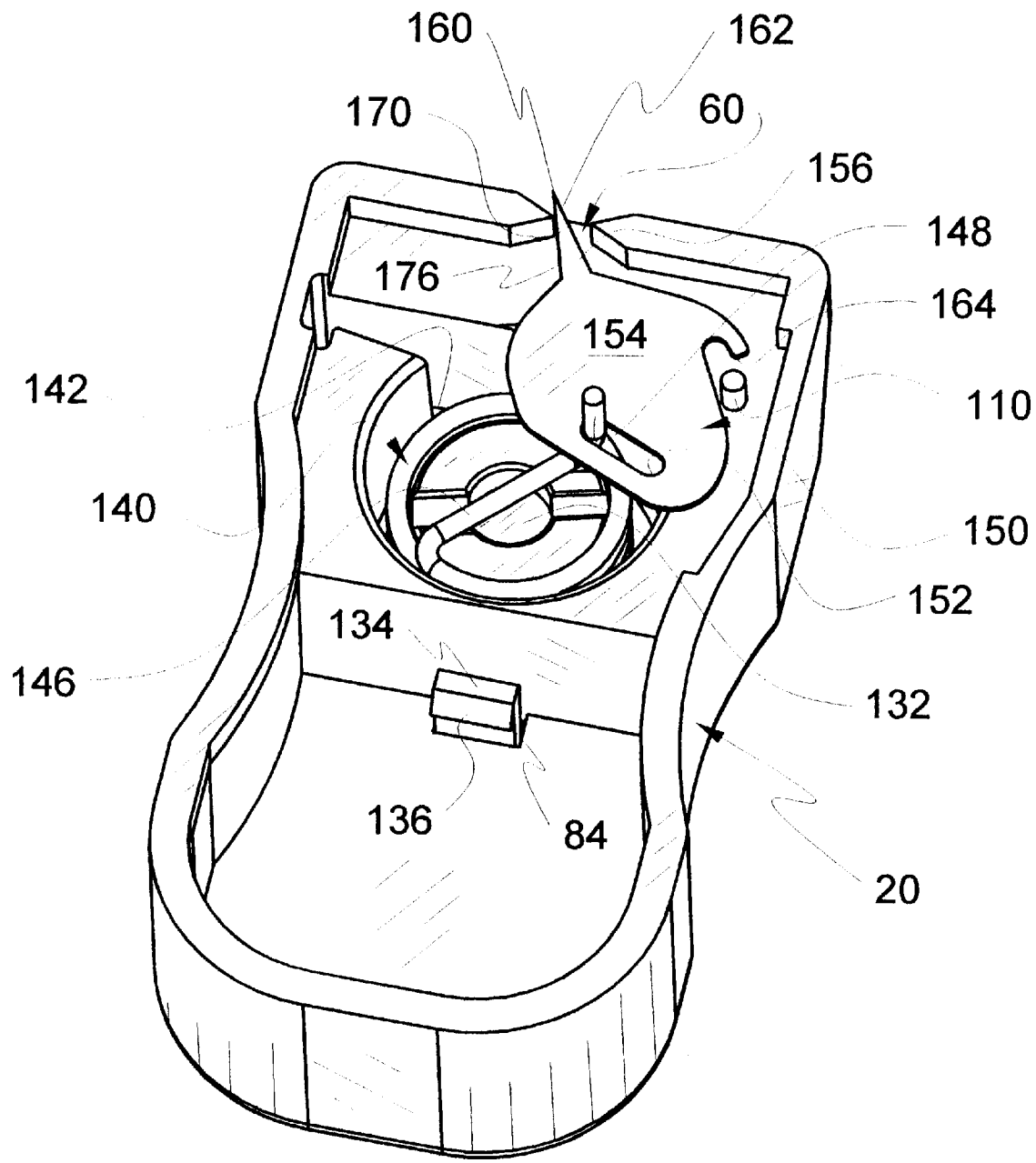
FIG. 10 is a perspective of the parts seen in FIG. 8 with the spring released from a cocked condition and the post partially rotated as the spring unwinds to deliver a sharpened point of the blade through a slot in the top part.

It should be noted that, when a tissue site (not shown) to be lanced is disposed against surface 52 (see FIG. 1), it can reasonably be expected that a portion of tissue surrounding the tissue site will conform to and at least partially bulge into slot 60 providing ready access for an extending sharpened point and associated blade segment 156. Lancet blade 150 is arcuately driven by travel of post 148 and sharpened point 160 is steered through slot 60 by interactive guidance provided by guide pin 110 and steering hook 164. In this manner, as sharpened point 160 is driven past abutment 170 and a portion of blade segment 156 is discharged obliquely (relative to the tissue site and surface 52) to commence a lancing cycle as seen in FIG. 10.

Figure 11:
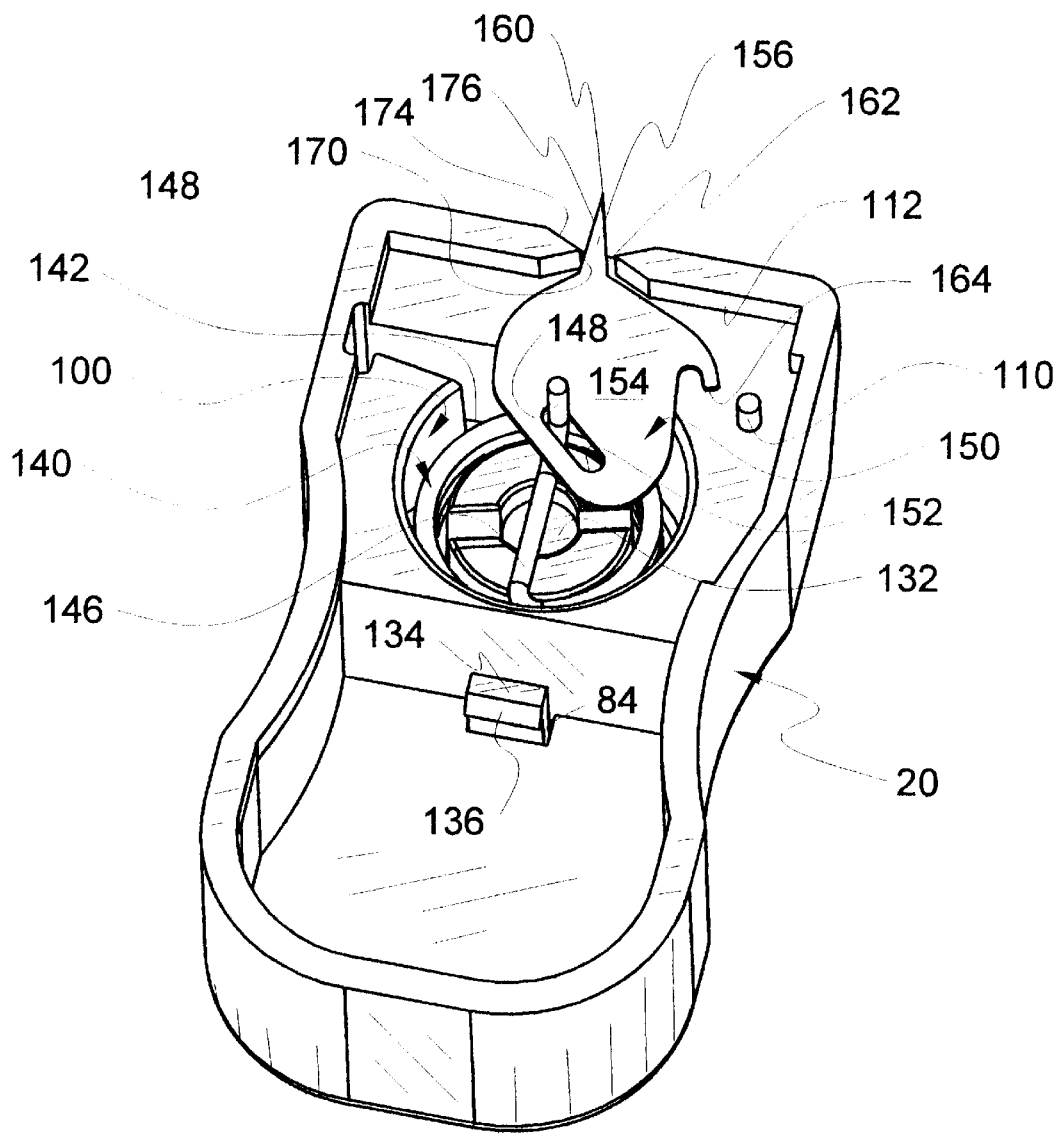
FIG. 11 is a perspective of the parts seen in FIG. 8 with the spring further unwound than in FIG. 10.
Figure 12:
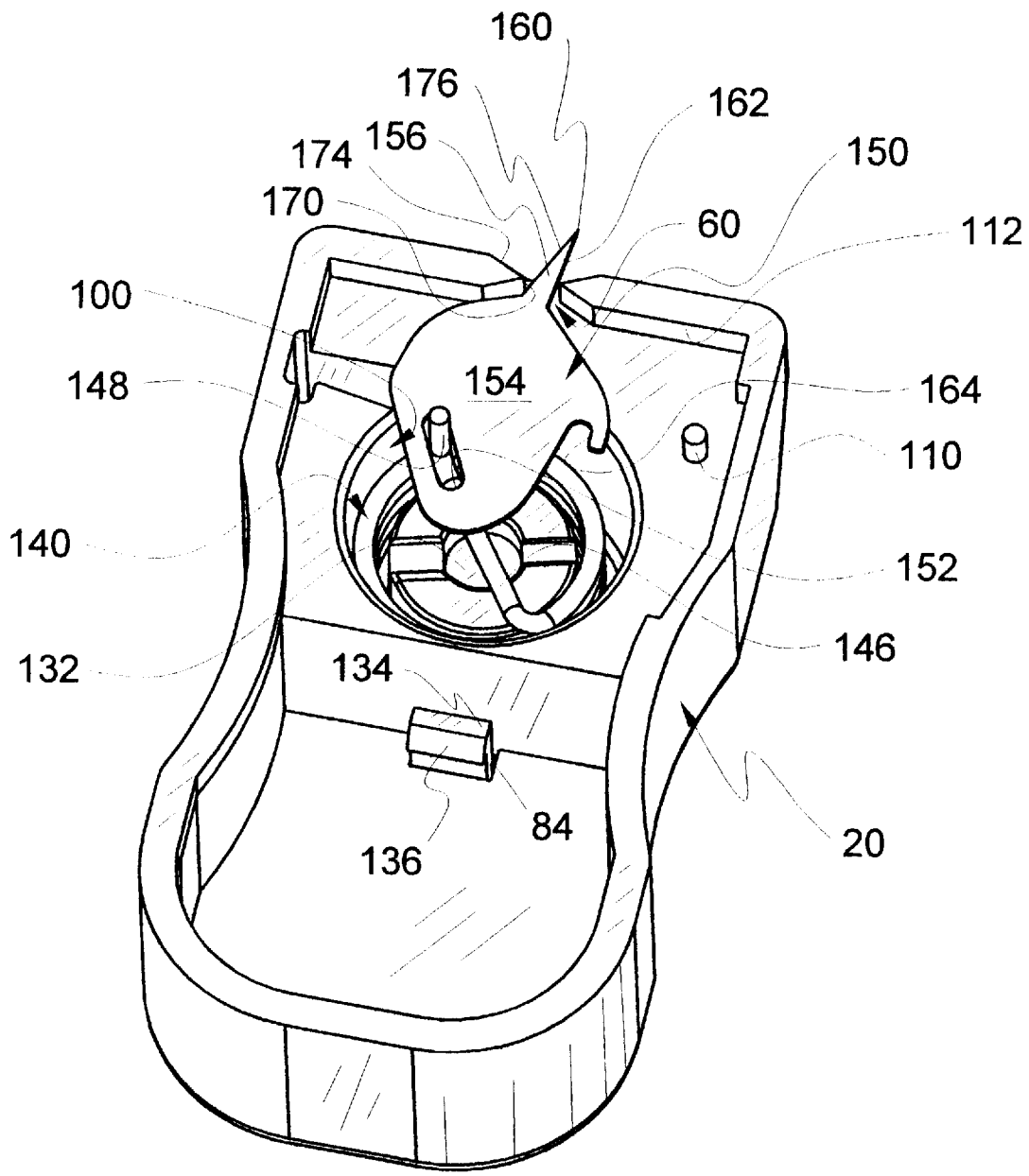
FIG. 12 is a perspective of the parts seen in FIG. 8 with the spring further unwound than in FIG. 11.
Figure 13:
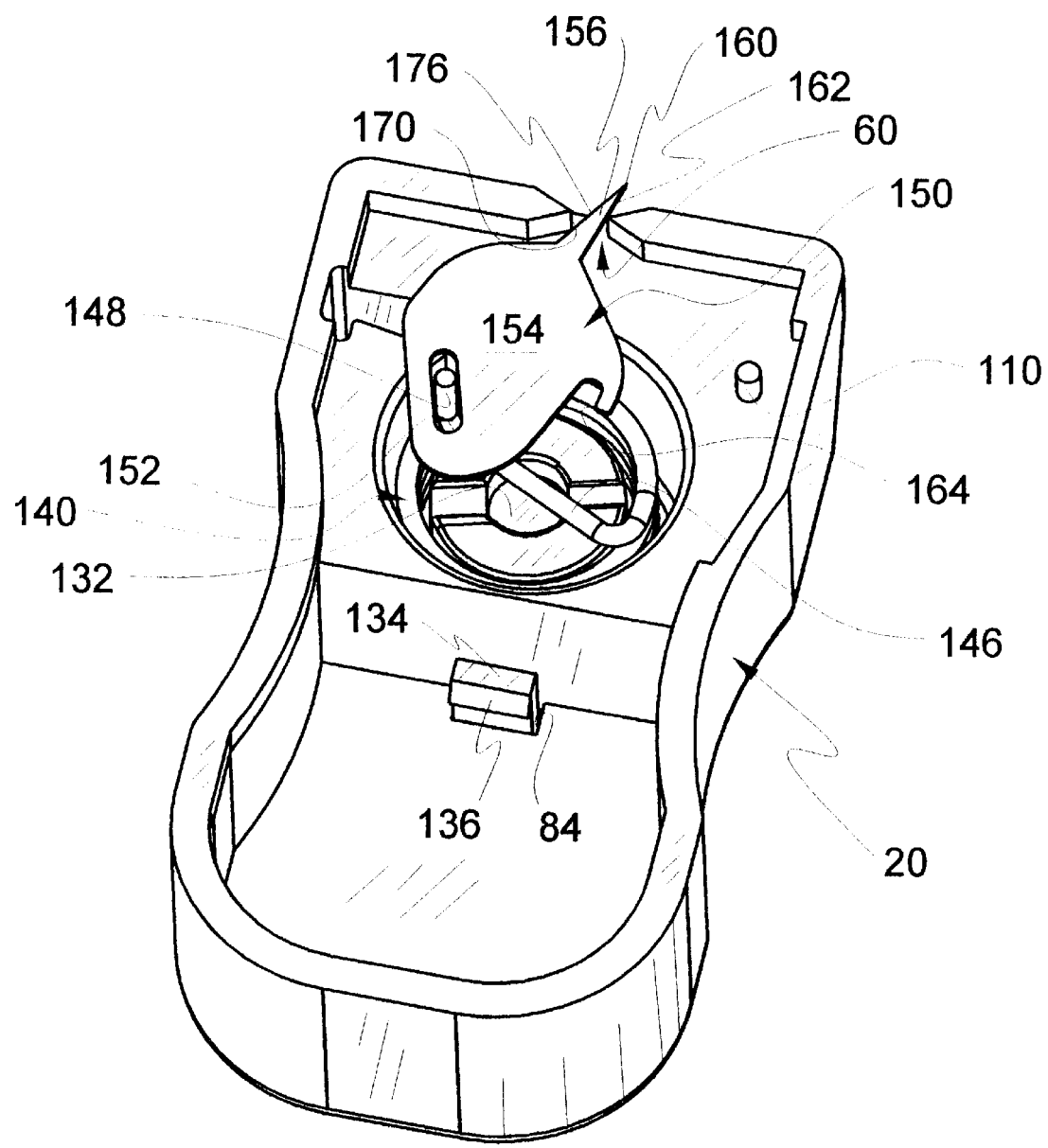
FIG. 13 is a perspective of the parts seen in FIG. 8 with the spring further unwound than in FIG. 12 to begin retracting the sharpened point back into the top part.

An ever broadening subsurface incision is made by blade segment 156 as sharpened edge 162 is displaced through tissue at the lance site as may be noted in FIGS. 11, 12 and 13. Note that the direction of lancing opposes the direction of angular travel of blade body portion 154. This rotation about abutment 170 produces an epidermal incision which is substantially the width of blade segment 156 at a maximum insertion point while the breadth of cut made along a line of traverse of sharpened point 160 is much broader than that blade width. It is for this reason that the blade segment should be made having as small a width as possible to reduce trauma to epidermal skin layers. However, it may be necessary to make anterior edge 176 somewhat thicker to displace tissue sufficiently for adequate blood flow.

Note also in FIGS. 12 and 13 that slot 152 is elongated to permit blade segment 156 to remain further distally extended as post 148 begins to be proximally displaced. Other slot configurations may be used within the scope of the invention to produce a variety of predetermined lancing patterns.

Figure 14:
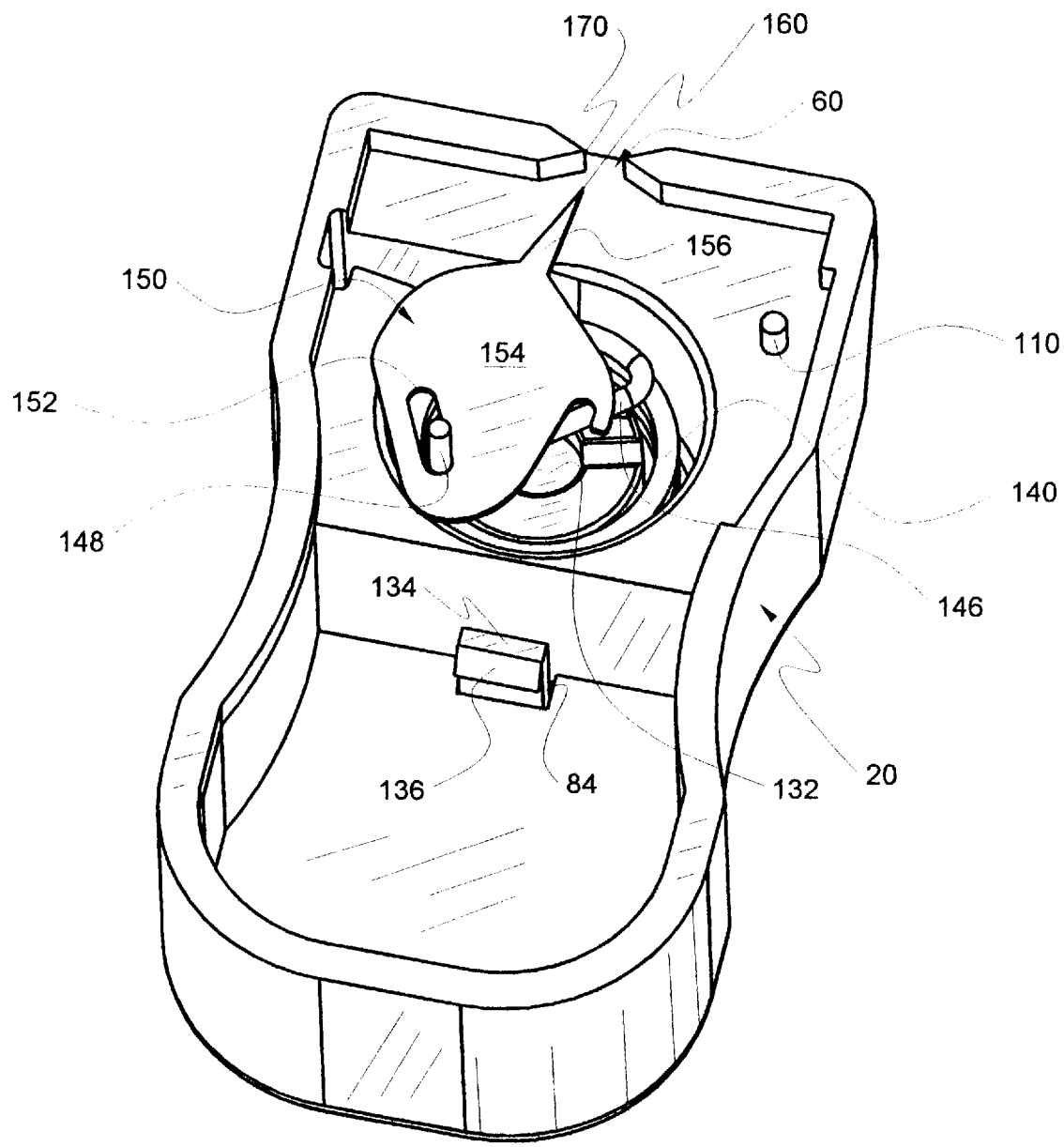
FIG. 14 is a perspective of the parts seen in FIG. 8 with the sharpened point fully retracted into the top part.
Figure 15:
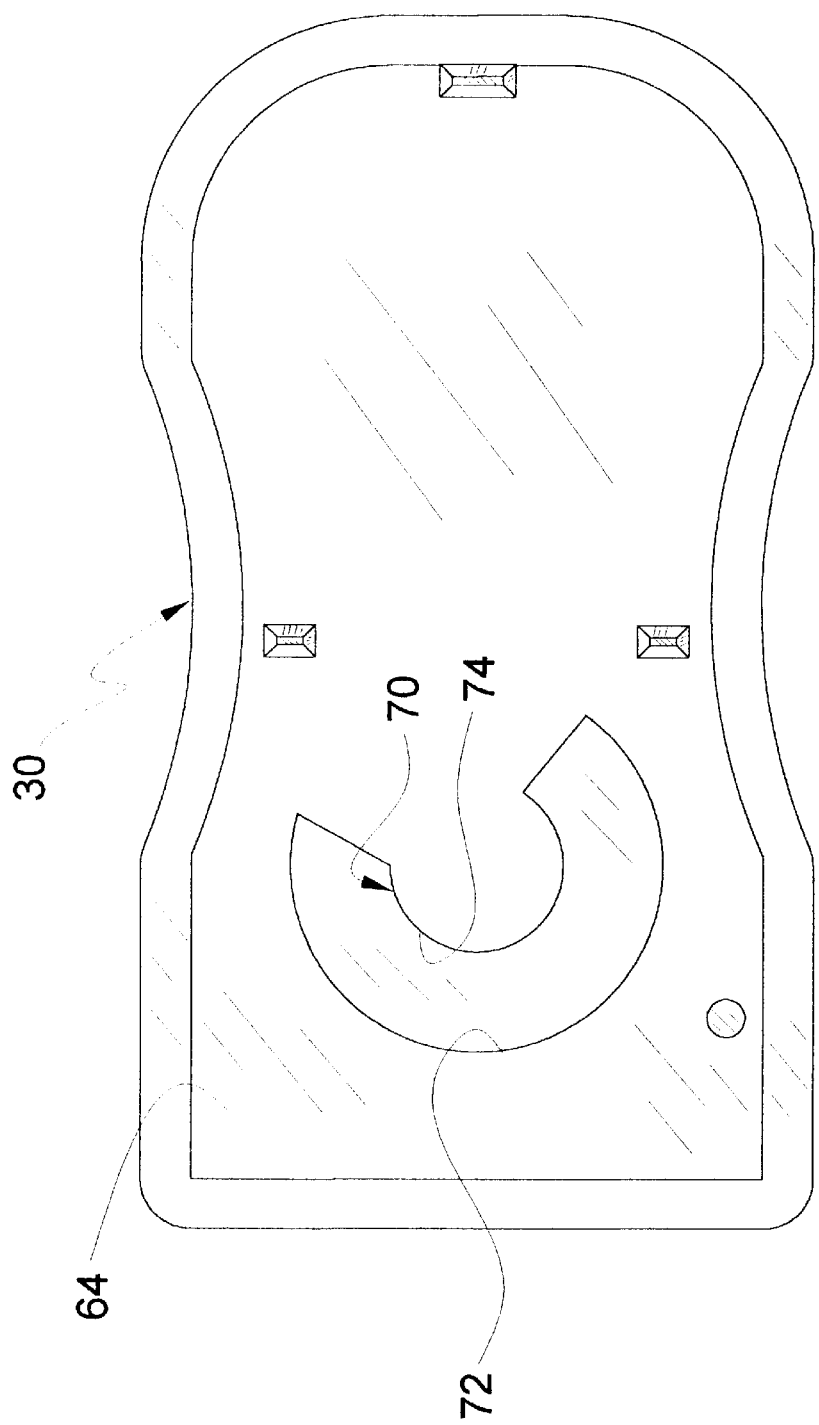
FIG. 15 is a superior elevation of the bottom part seen in FIG. 2 showing the shape of a guide track which controls travel of a spring post and consequently the lancet blade to a predetermined lancing pattern.

Finally, post 148 is displaced to be in contact with a proximal portion of slot 152 and lancet blade 150 is fully retracted, as seen in FIG. 14, for safe disposal. It may be desired to constrain blade 150 to a different lancing pattern than that disclosed in FIGS. 10–14. As mentioned above, channel 70, as seen in FIGS. 2 and 15, is formed to guide post 148 through a natural arc which corresponds to angulation of arm 146 as torsion spring 140 unwinds. Edges 72 and 74 form a track which limits extension of blade segment 156 and thereby controls with precision the pattern of each lancing incision.

Figure 16:
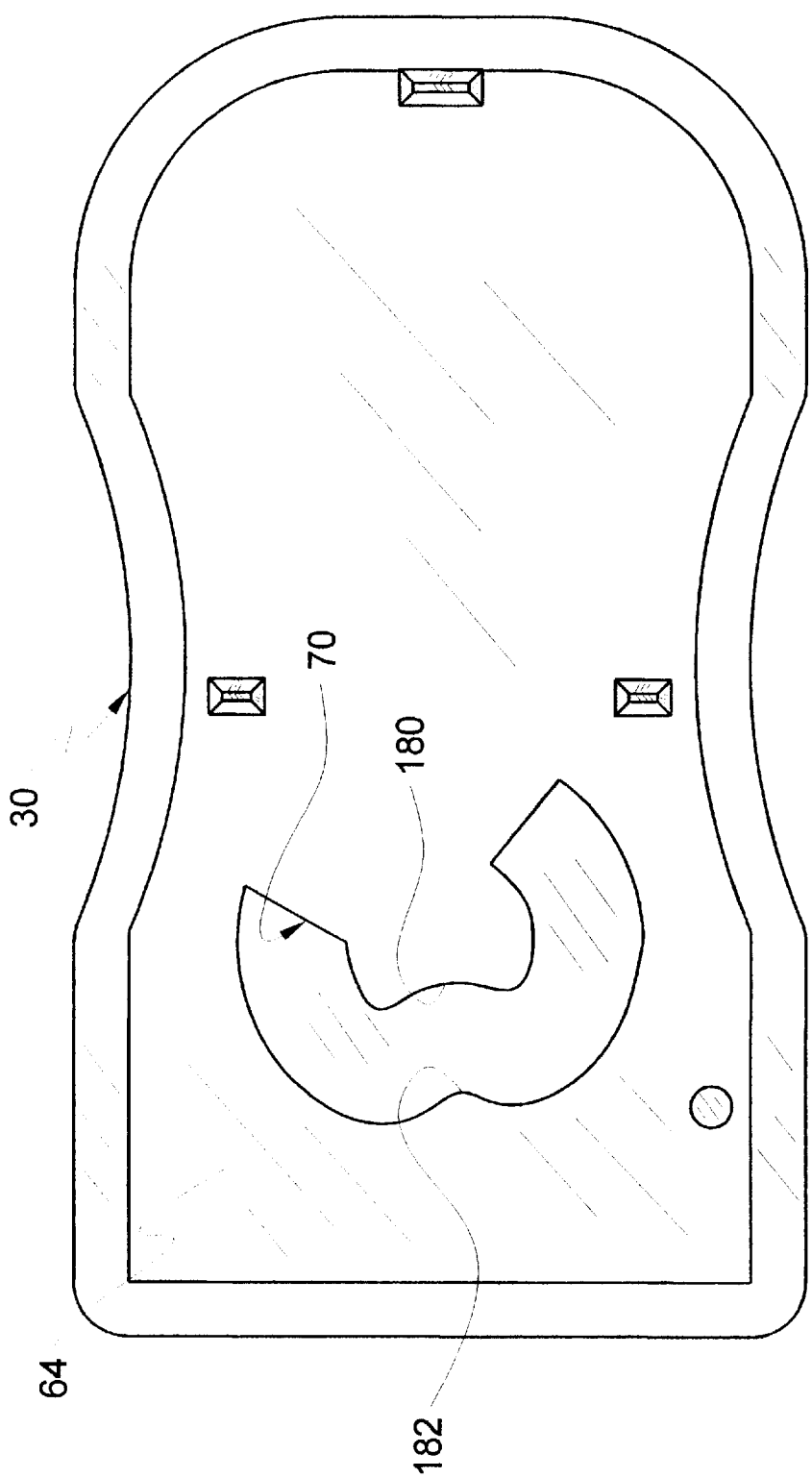
FIG. 16 is a section of a bottom part similar to the bottom part seen in FIG. 15, but having a differently shaped guide track to predetermine a different guide pattern.

Other patterns than those which follow a path of natural displacement of arm 146 may also be implemented within the scope of the instant invention as is exemplified by a guide track (also numbered 70 per the general connotation indicated earlier), which is seen in FIG. 16. Guide track 70 in FIG. 16 comprises arcuate sides 180 and 182. Medially sides 180 and 182 are proximally displaced relative to sides 72 and 74 seen in FIG. 15. Such displacement causes post 148 to follow an abnormal pattern which might cause binding unless a portion of torsion spring 140 is displaced proximally as well. Such a displacement is possible as coil 144 may be readily deformed to accommodate the displacement as post 148 travels along track 70.

Figure 17:
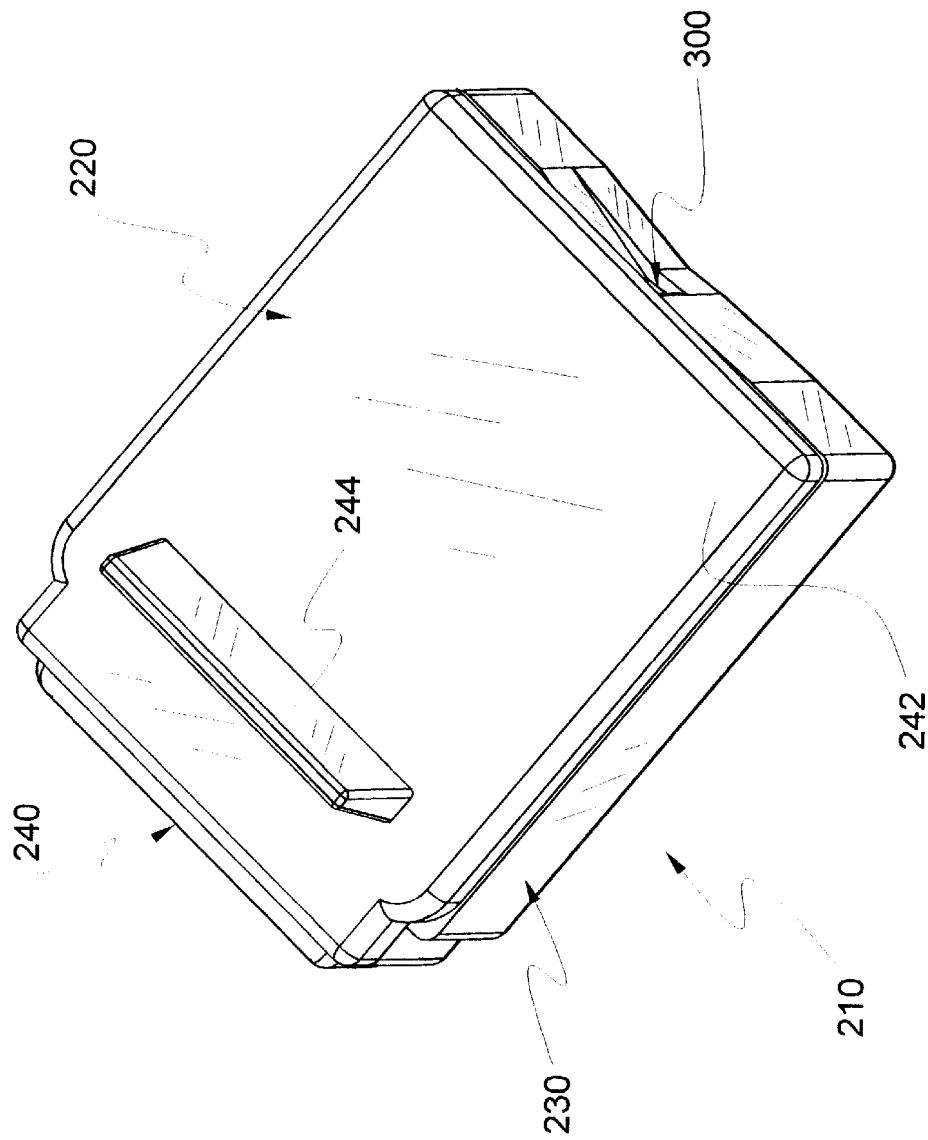
FIG. 17 is a perspective of an assembly of a second embodiment of the instant invention.

A second embodiment of the instant invention is illustrated in FIGS. 17–25. An assembly 210 of the second embodiment is seen in FIG. 17. Assembly 210 comprises a top cover 220, a bottom part 230 and an actuator 240. Generally cover 220 is formed to accomplish a tight aseptic seal when affixed to bottom part 230 and provides a generally planar exterior surface 242 for one side of assembly 210. An elongated wing 244 rises transversely from surface 242 to provide a first handle for facilely gripping assembly 210. A complementary second handle is disposed on a side of bottom part 230 opposite surface 242, but is not shown. By placing an index finger against one handle and a forefinger against the other handle, as an example, assembly 210 may be disposed against a site to be lanced and actuator 240 depressed with a thumb of the same hand, permitting facile one-handed operation.

Figure 18:
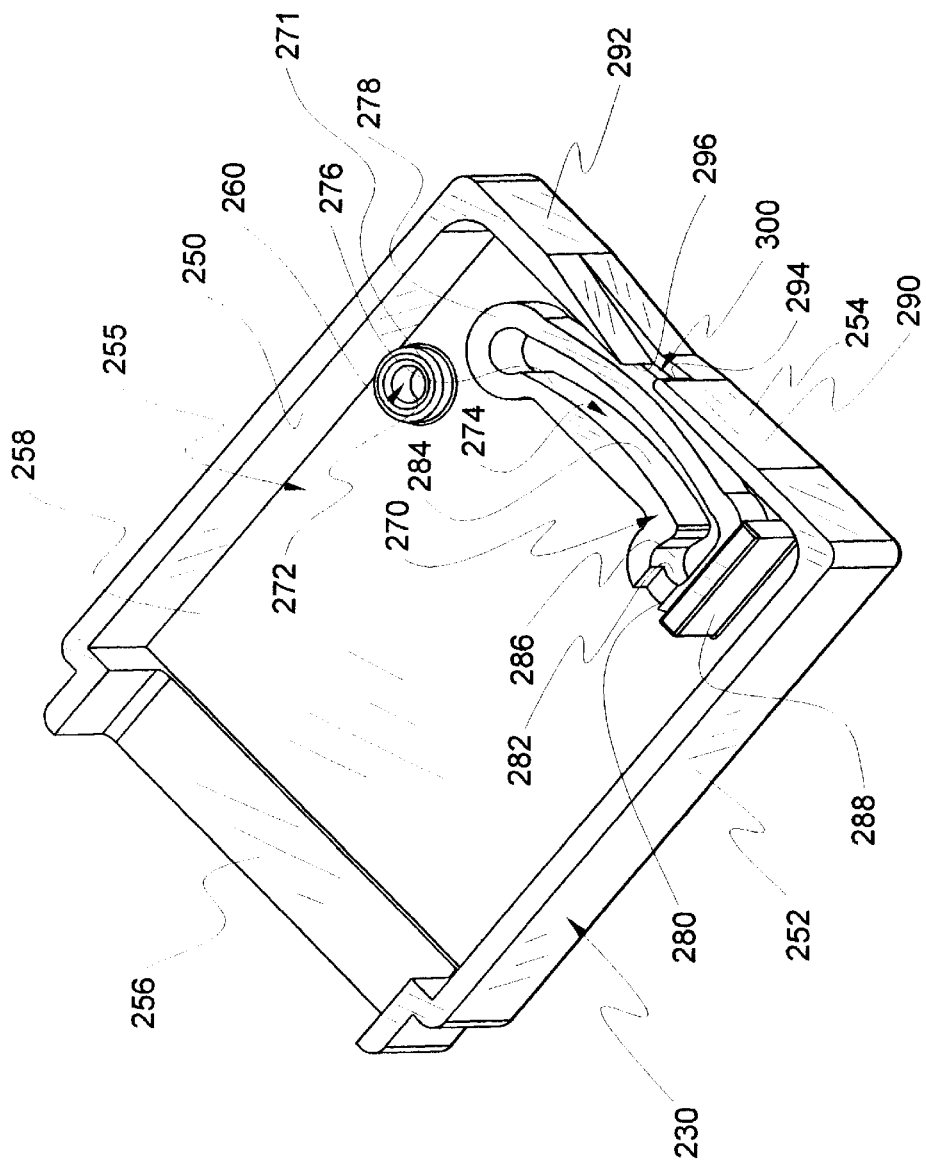
FIG. 18 is a perspective of a bottom part of the assembly seen in FIG. 17.

A perspective inside view of bottom part 230 is seen in FIG. 18. Part 230 comprises a pair of elongated upright sides 250 and 252 which are interconnected by a front face 254 to form a tray-like container 255 having an open proximally disposed entry site 256 for an actuator button, to be described hereafter, and a planar floor 258. Distally disposed within container 255 are a spring arm anchor 260 and a spring lock and guide assembly 270. Anchor 260 comprises a raised outer ring 271 and a centrally disposed aperture 272 wherein a post of a locking arm of a spring is rotatably disposed. Details related to the spring are addressed in detail hereafter.

Guide assembly 270 comprises an arcuate closed wall structure 274 forming a track 276 wherein a post of another arm of the spring is guided. The purpose and result of guiding the post of the other spring arm is disclosed in detail hereafter. Structure 274 comprises a substantially planar superior surface 278 which is interrupted by a proximally disposed channel 280. Channel 280 is proximal to a portion 282 of track 276 which is displaced proximally from a larger more transversely disposed segment 284. Proximally disposed within portion 282 is a medially inclined indentation 286 in wall structure 274 which acts as a catch for the post of the other arm of the spring. Laterally disposed to track 276 is a structure 288 which rises substantially above surface 278.

Front face 254 comprises a pair of aligned walls 290 and 292. In combination, walls 290 and 292 comprise juxtaposed frame members 294 and 296, respectively, which form an opening 300 which provides an exit and reentry passageway 300 for a lancet blade. For reasons which are fully clarified hereafter in disclosure related to patterns of travel of lancet blades, it is preferred that frame 296 be formed to be as sharp an edge as is reasonably moldable while maintaining sufficient structural strength to prevent undesirable deformation.

Figure 19:
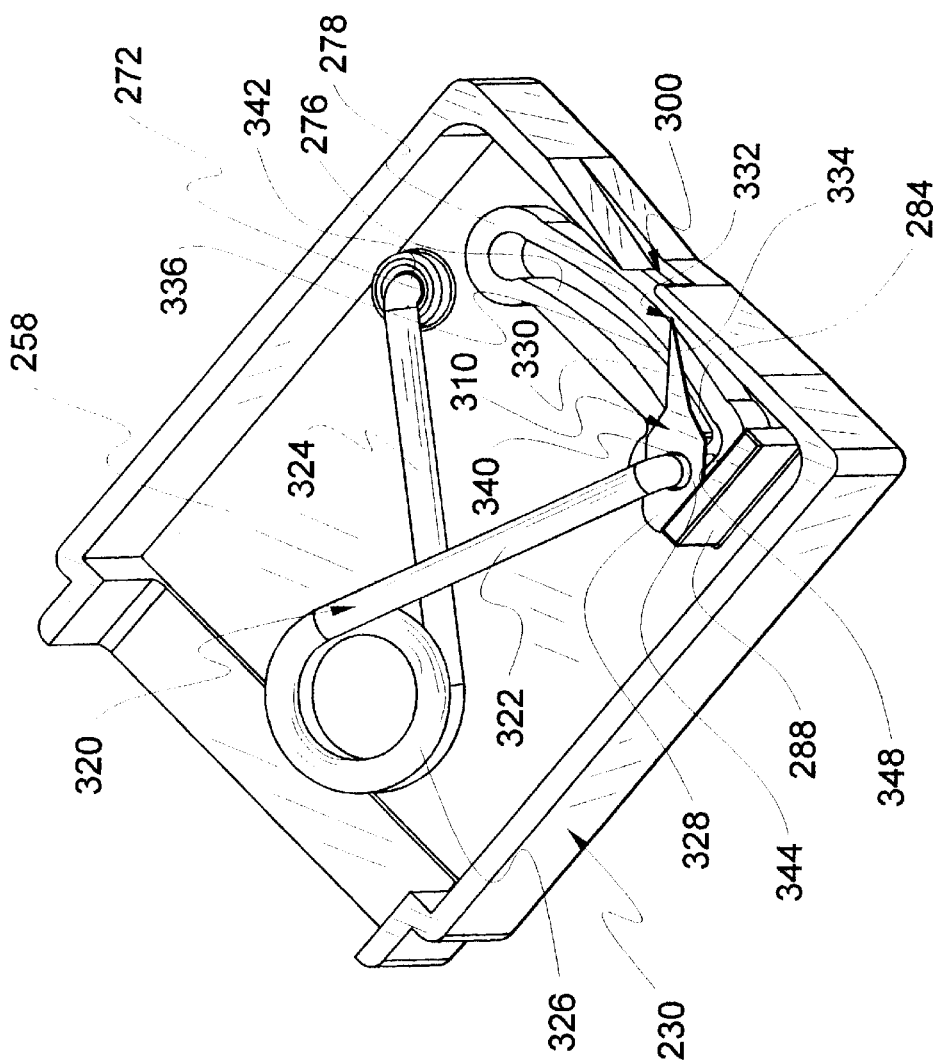
FIG. 19 is a perspective of the bottom part seen in FIG. 18 with a torsion spring and lancet blade disposed therein.

Reference is now made to FIG. 19, wherein a lancet blade 310 and a torsion spring 320 are disposed in bottom part 230. Torsion spring 320 comprises a first arm 322, a second arm 324 and a spring coil 326. Lancet blade 310 comprises a blade body portion 328 and a blade segment 330, blade segment 330 being similar in form and function to blade segment 156. Similar to blade segment 156, blade segment 330 comprises a sharpened point 332, a sharpened edge 334 and an anterior edge 336. Rather than a slot, as found in blade body portion 154, blade body portion 328 comprises a substantially round orifice 340.

The second arm 324 of spring 320 comprises a substantially transverse bend at a free end 342 which is disposed in aperture 272 to securely anchor arm 324 thereat. A post 344 formed by a transverse bend in first arm 322 of spring 320 is disposed through orifice 340 and securely, but releasibly anchored by disposition in indentation 286 in wall structure 274, see FIG. 18.

Figure 22:
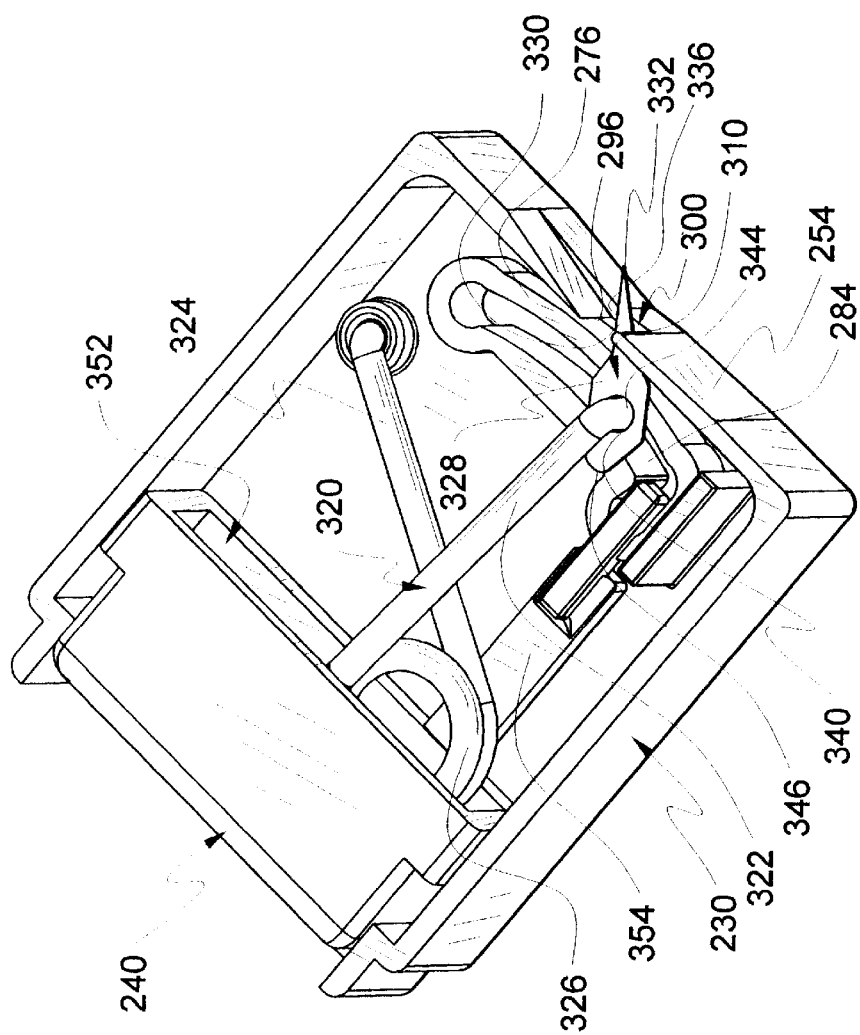
FIG. 22 is a perspective of the combination of parts seen in FIG. 21 wherein an arm of the torsion spring and the lance blade are displaced to drive the lancet blade obliquely through a slot in the bottom part.

Further, blade body portion 328 comprises a substantially straight edge 346 (as seen in FIG. 22) which affords a flat against which a substantially planar surface 348 of structure 288 acts to retard rotation of lancet blade 310. As will be evident hereafter, surface 348 not only retards rotation while arm post 344 is anchored in indentation 286, but also acts as a guide urging sharpened point 332 into and through opening 300 as post 344 is displaced into segment 284 of track 276.

Figure 20:
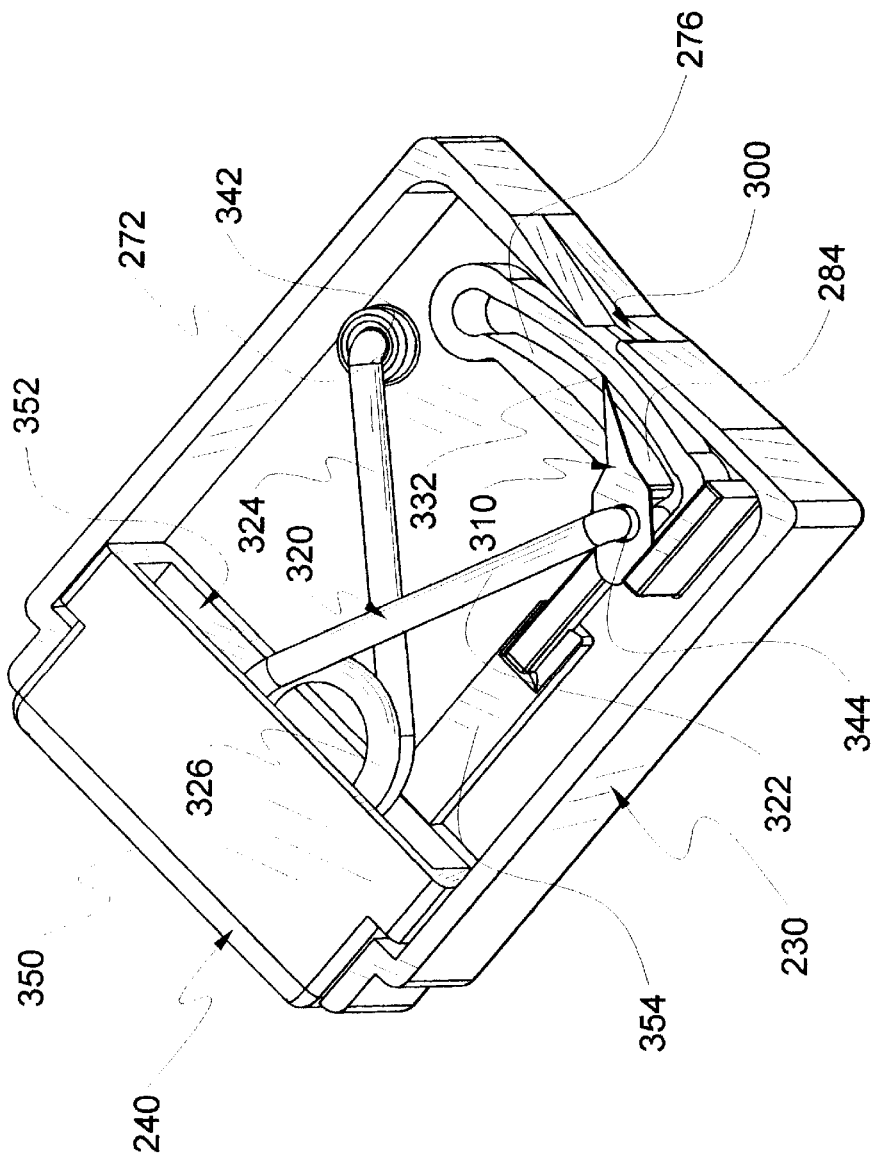
FIG. 20 is a perspective of the combination seen in FIG. 19 with an actuator assembled therewith.

Reference is now made to FIG. 20, wherein actuator 240 is seen to comprise a depressible button 350, a hollow section 352 (in which spring coil 326 partially resides while the spring is cocked) and an elongated leg 354 which extends from hollow section 352 to close juxtaposition with post 344 of arm 322. Leg 354 is sized to be stabilized and guided by channel 280 (see FIGS. 18 and 21). Note that spring coil 326 and therefore torsion spring 320 is restrained from undue twisting while disposed in hollow section 352.

Figure 21:
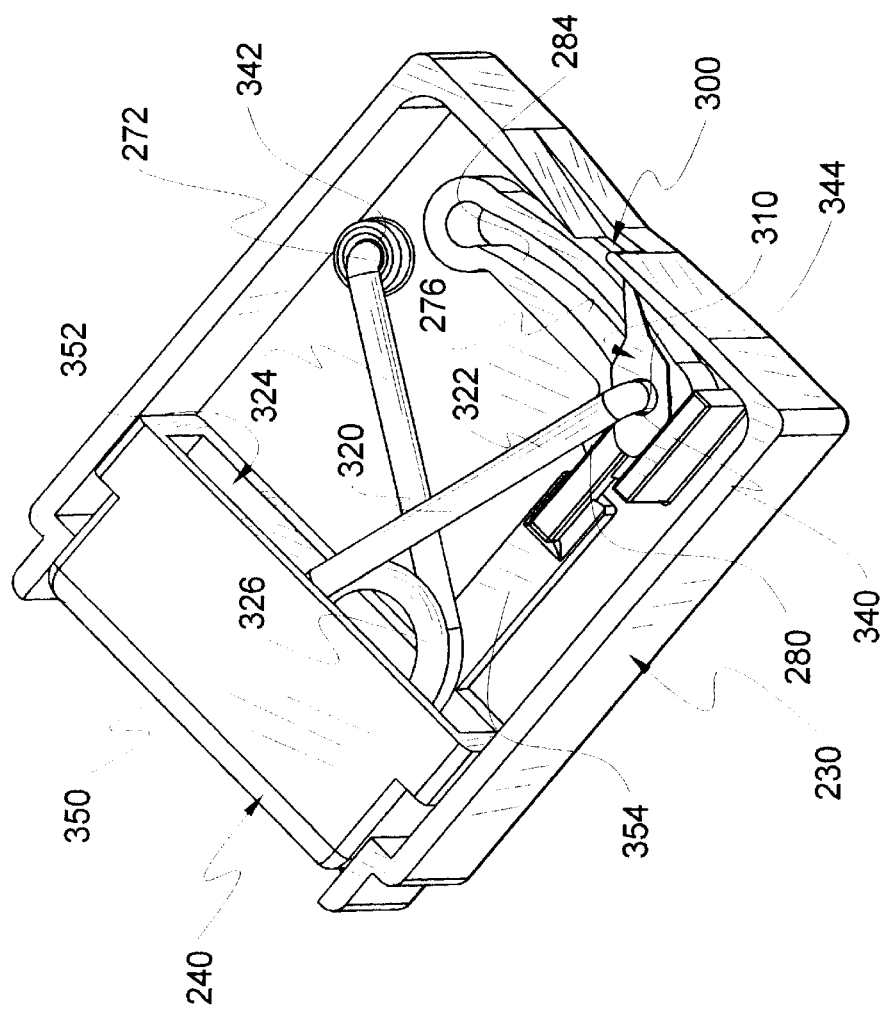
FIG. 21 is a perspective of the combination of parts seen in FIG. 20 wherein the actuator is displaced to initiate a lancing cycle.

Depressing actuator 240 distally forces post 344 from its anchored position at indentation 286 toward and into segment 284 of track 276, as seen in FIG. 21. Sharpened point 332 is forced into juxtaposition relative to opening 300. As post 344 is displaced into segment 284, arm 322 reactively follows track 276 toward arm 324.

As seen in FIG. 22, blade segment 330 exits through opening 300 at an oblique angle relative to front face 254. Direction of travel of lancet blade 310 and post 344 disposes anterior edge 336 of blade segment 330 into sliding contact with frame member 296 such that lancet blade 310 is angularly displaced relative to front face 254 and opening 300 along a line from orifice 340 to frame member 296. Note that this displacement defines an arc of travel of the sharpened point which is substantially longer than the width of blade segment 330 at its greatest extension from surface 254. Note also that, should a skin surface of a patient be disposed to protrude or bulge into opening 300, the length of an epidermal layer cut is substantially less than the length of the associated cut through the dermal layer as determined by travel of sharpened point 332. In this manner, there is less trauma at skin surface than the concurrent length of cut in subsurface (capillary rich) tissue in sub-epidermal layers.

Figure 23:
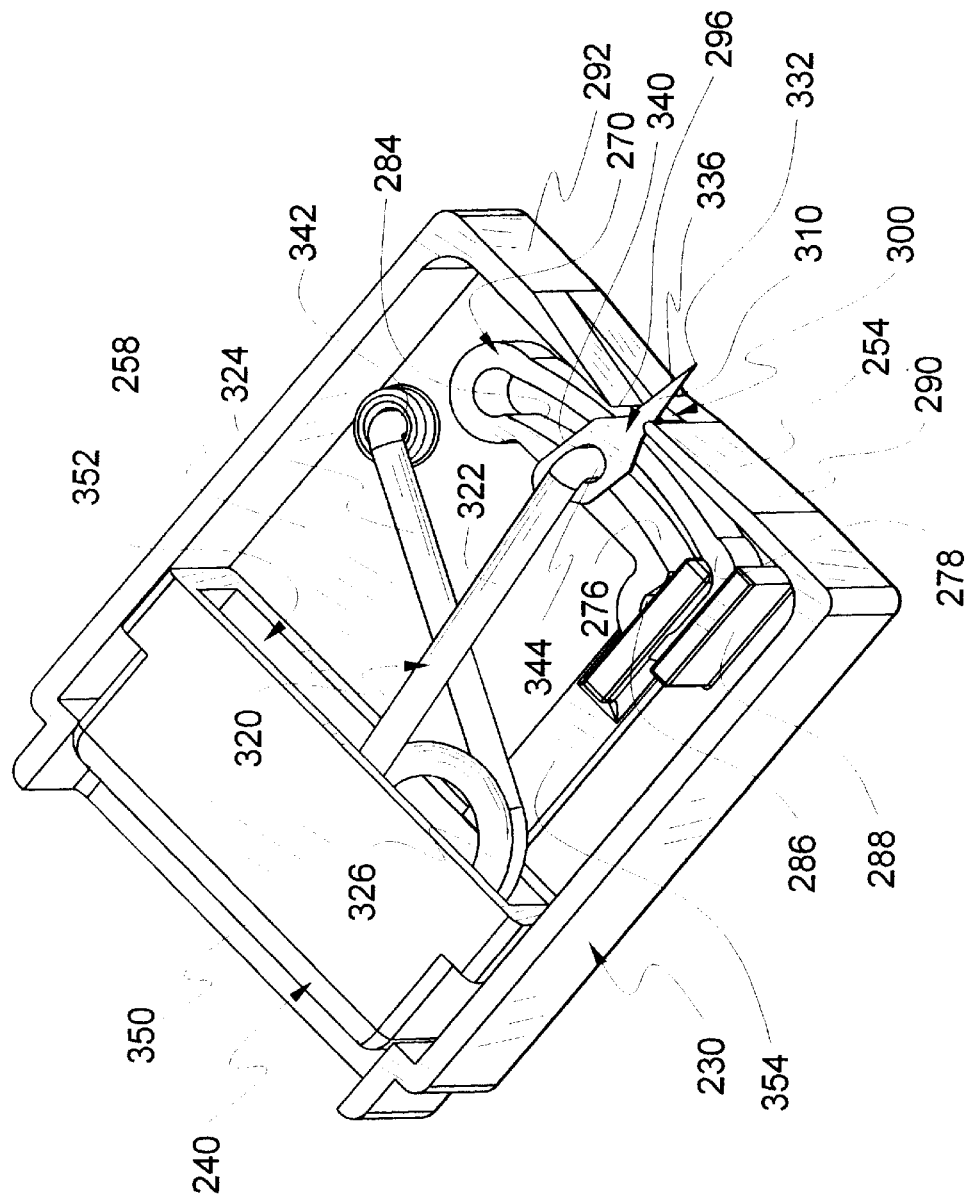
FIG. 23 is a perspective of the combination of parts seen in FIG. 22 wherein the arm and lancet blade are still further displaced.
Figure 24:
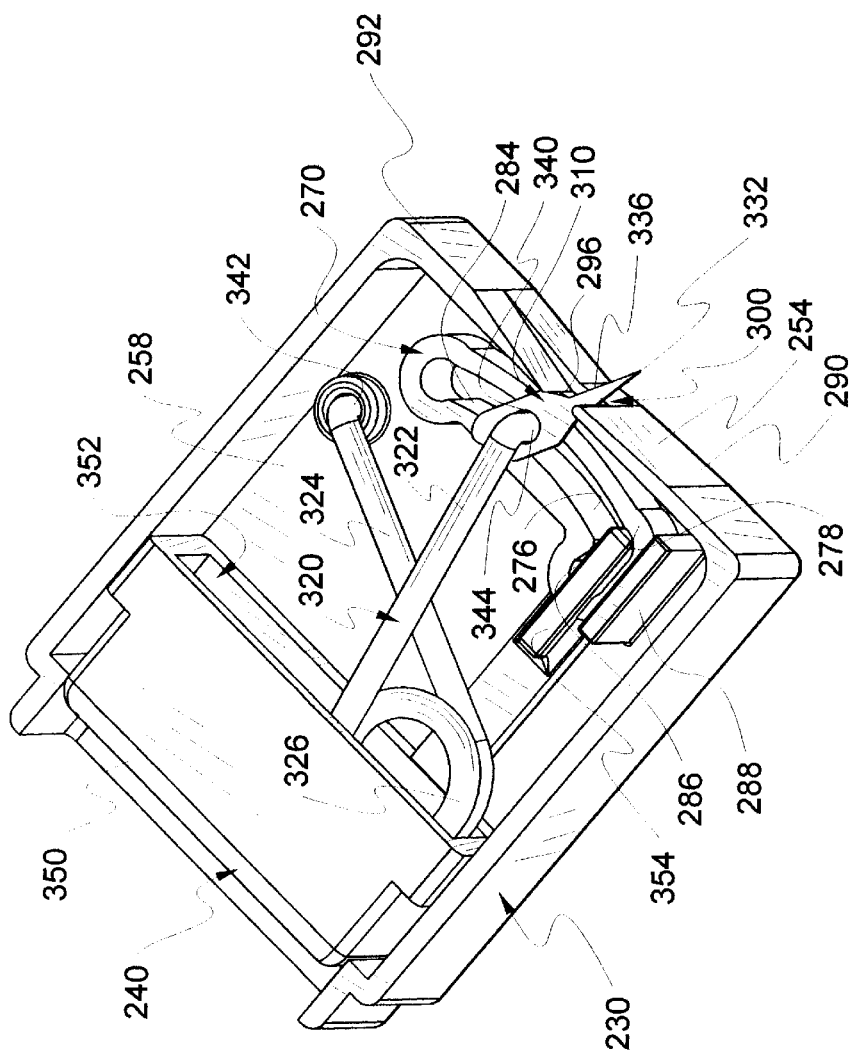
FIG. 24 is a perspective of the combination of parts seen in FIG. 23 wherein the arm and lancet blade are yet further displaced.

Reference is now made to FIGS. 23 and 24 wherein lancet blade 310 is seen to rotate to drive sharpened point ever more acutely toward wall 290 to broaden the path of deep incision. The depth of cut is determined by the angulation of segment 284 of track 276. An incision of nearly constant depth may be achieved by changing the substantially concave shape of track 276 to a planar or convex shape. Note that post 344 and arm 322 are free to follow such a track 276 shape as coil 326 floats freely. Coil 326 of spring 320 is permitted to be displaced by action of arms 322 and 324 as spring 320 unwinds. In this manner, travel of lancet blade 310 is entirely determined by disposition of post 344 in track 276 and action of anterior edge 336 against frame member 296.

Figure 25:
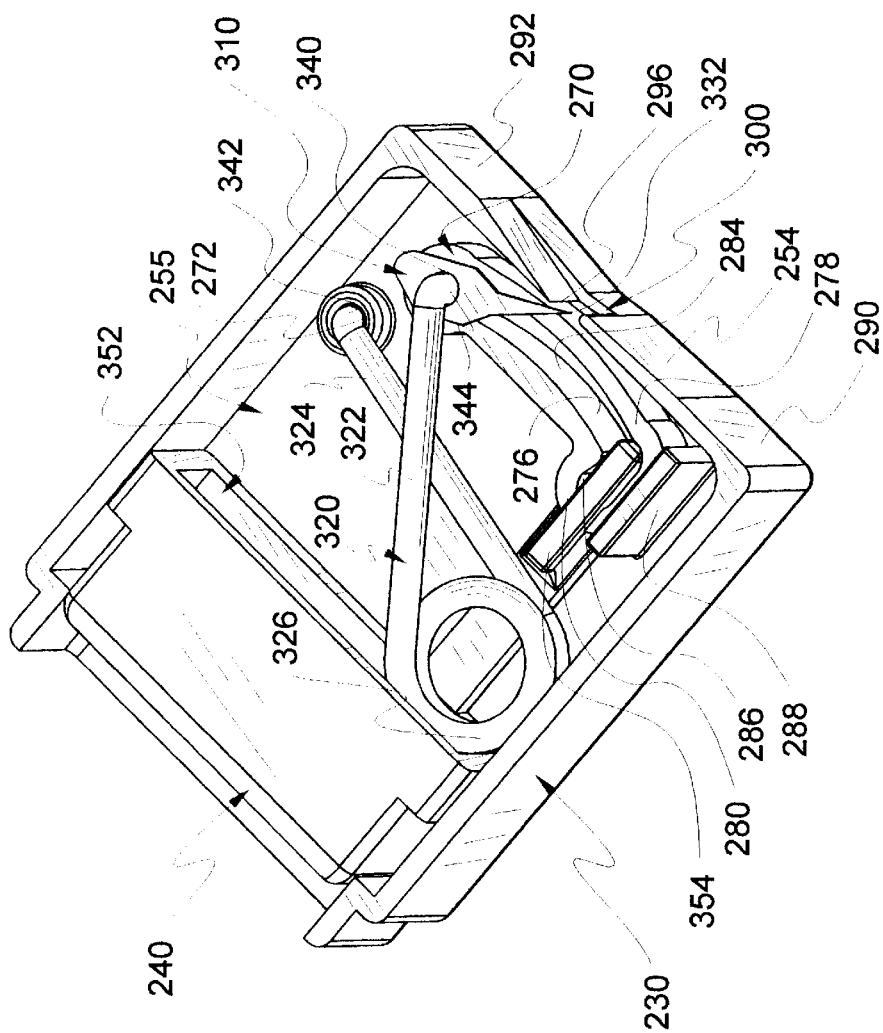
FIG. 25 is a perspective of the combination of parts seen in FIG. 24 wherein the arm is further displaced and the lancet blade is fully retracted into the bottom part.

As seen in FIG. 25, lancet blade 310 is completely retracted into container 255 when post 344 reaches the end of track 276. For this purpose, spring 320 should retain a bias when post 344 reaches the end of track 276. At this point, lancet blade 310 is totally protected and thereby made safe for disposal.

Parts 220, 230 and 240 may be made from the same materials as those indicated herebefore for parts 20, 30 and 40, respectively. Injection molding of these parts is preferred. However, 0.040 inch stainless steel or treated (e.g. with silicone) piano wire is preferred for torsion spring 320.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A one-time-use, self-powered lancet apparatus comprising:

a housing comprising a hollow space for fully containing a lancet blade member, and an open frame forming a slot through which a blade portion of the lancet blade member is extended and retracted;

the lancet blade member which comprises a proximally disposed planar portion having an aperture for communicating with an energy-storing memory element and a distally disposed elongated thin blade section having a sharpened tip and at least one sharpened edge;

the energy storing memory element comprising a latching member by which the element is retained in an energy storing state and a part which is displaced as stored energy is released, said part being disposed to communicate with the aperture;

a lancet actuation mechanism comprising a releasible catch which displaceable within the housing to releasibly restrain the latching memory element and an element is displaced to release the latching member to free the energy storing member to initiate a lancing procedure; and said frame comprising a side abutment, said energy storing memory element comprising an energy release vector and said blade section comprising a blade edge such that, when the energy storing memory element is freed and displaces the proximal portion in a given direction, the blade edge communicates with the side abutment to displace the blade section disposed within the frame in an arcuate direction opposite to the given direction such that a resulting lancing incision has a characteristic pattern having a smaller cut at the surface of the incision than in the subsurface thereof.

2. A lancet apparatus according to claim 1 wherein the energy storing memory element comprises a spring.

3. A lancet apparatus according to claim 2 wherein the spring comprises a torsion spring.

4. A lancet apparatus according to claim 3 wherein said torsion spring comprises a post which communicates with the aperture.

5. A lancet apparatus according to claim 1 wherein said housing comprises a hub which comprises a groove which is the catch.

6. A lancet apparatus according to claim 1 wherein said latching member and said part are integral.

7. A lancet apparatus according to claim 1 wherein said lancet actuation mechanism comprises a button disposed to be displaced transversely relative to a plane of the blade member.

8. A lancet apparatus according to claim 1 wherein said lancet actuation mechanism comprises a slider which is displaced parallel to a plane of the blade member.

9. A lancet actuating apparatus according to claim 1 wherein said housing comprises a guide track which communicates with said displaced part to restrictively control breadth and depth of the pattern.

10. A method of lancing comprising the steps of:

providing a lancet actuating apparatus comprising:

a housing having a side which is disposed against a site to be lanced during a lancing procedure, said side comprising a blade exit and reentry slot;

a lancet blade component safely disposed within said housing prior to use in the lancing procedure, said component comprising a proximally disposed portion which remains in the housing during the lancing procedure and a blade, having a sharpened tip and at least one cutting edge, at least a segment of said blade exits the housing to perform a lancing procedure and returns to the housing for safe disposal;

an energy storing memory element which, when actuated, communicates with said proximally disposed portion to urge the blade through a predetermined lancing pattern outwardly and then inwardly through the blade exit and reentry slot;

a lancet actuating mechanism comprising a release trigger which activates the energy storing memory element;

placing the apparatus against a site to be lanced;

triggering release of the energy storing memory element which subsequently communicates with the proximally disposed portion to accomplish the following steps:

forcibly steering the proximally disposed portion to guide the blade obliquely outward through the slot;

rotating the blade laterally about an edge of the slot under influence of the memory element and, thereby, displacing the proximally disposed portion in a first direction relative to said slot while at the same time displacing the blade in a direction opposite the first direction such that the sharpened tip and cutting edge produce a smaller incision in a surface of the site being lanced than in a subsurface thereof;

returning the blade into the housing.

11. A method according to claim 10 wherein said housing comprises a guide track and said energy storing memory element comprises a track follower and which act in combination during the rotating step thereby restricting the depth of the lance in the subsurface as the blade rotates in the opposite direction.

12. A method according to claim 10 wherein said forcibly steering and rotating steps comprise partially unwinding a torsion spring.

13. A lancet apparatus comprising:

a housing comprising a frame about an opening through which a lancet is extended and retracted and against which a site to be lanced is disposed during a lancing procedure;

the lancet comprising an elongated, thin knife-like blade and a sharpened point;

an energy storing memory element which, when actuated, communicates with the lancet to urge the blade through a predetermined lancing pattern outwardly and then inwardly through the opening;

a mechanism comprising a trigger for actuating the energy storing memory element;

a segment of said frame acting as a fulcrum against said blade to constrain entry of the blade into the entry site to a breadth of cut which is substantially the same as the maximum width of the portion of blade inserted into the site.

* * * * *